(12) United States Patent
Powers et al.

(10) Patent No.: US 9,097,604 B2
(45) Date of Patent: Aug. 4, 2015

(54) ELECTRODYNAMIC MODAL TEST IMPACTOR SYSTEM AND METHOD

(71) Applicant: The Boeing Company, Seal Beach, CA (US)

(72) Inventors: Donald E. Powers, Federal Way, WA (US); Jason C. Kiiskila, Kent, WA (US)

(73) Assignee: The Boeing Company, Chicago, IL (US)

( * ) Notice: Subject to any disclaimer, the term of this patent is extended or adjusted under 35 U.S.C. 154(b) by 324 days.

(21) Appl. No.: 13/691,584

(22) Filed: Nov. 30, 2012

(65) Prior Publication Data
US 2014/0150526 A1    Jun. 5, 2014

(51) Int. Cl.
*G01N 3/30* (2006.01)
*G01M 7/08* (2006.01)
*G01N 3/34* (2006.01)
*G01N 29/04* (2006.01)
*G01N 29/12* (2006.01)
*G01N 3/317* (2006.01)

(52) U.S. Cl.
CPC . *G01M 7/08* (2013.01); *G01N 3/34* (2013.01); *G01N 29/045* (2013.01); *G01N 29/12* (2013.01); *G01N 3/30* (2013.01); *G01N 3/317* (2013.01); *G01N 2203/0039* (2013.01); *G01N 2291/042* (2013.01); *G01N 2291/2694* (2013.01)

(58) Field of Classification Search
CPC .... G01N 3/30; G01N 2203/0039; G01M 7/08
USPC ............................ 73/12.09, 12, 579, 649, 588
See application file for complete search history.

(56) References Cited

U.S. PATENT DOCUMENTS

| | | | |
|---|---|---|---|
| 2,289,962 A | 7/1942 | Hancock | |
| 4,682,490 A * | 7/1987 | Adelman et al. | 73/12.09 |
| 5,048,320 A * | 9/1991 | Mitsuhashi et al. | 73/12.09 |
| 6,194,796 B1 * | 2/2001 | Yeakley | 310/14 |
| 2007/0096568 A1 * | 5/2007 | Patt et al. | 310/15 |

FOREIGN PATENT DOCUMENTS

| | | |
|---|---|---|
| KR | 20030068351 A | 8/2003 |
| WO | WO2008156515 A2 | 12/2008 |

OTHER PUBLICATIONS

Georgeson, G., et al., "Electronic Tap Hammer for Composite Damage Assessment", Nondestructive Evaluation of Aging Aircraft, Airports and Aerospace Hardware, Proceedings of SPIE vol. 2945, pp. 328-338, Dec. 3-5, 1996 (10 pages).

(Continued)

*Primary Examiner* — Lisa Caputo
*Assistant Examiner* — Nathaniel T Woodward

(57) ABSTRACT

There is provided an electrodynamic modal test impactor system and method. The system has a controller device and an impactor assembly coupled to the controller device. The impactor assembly has a housing and a permanent magnet positioned within the housing. The impactor assembly further has a voice coil positioned within the housing in a magnetic gap of a magnetic yoke housing. The voice coil is driven by the controller device. The impactor assembly further has a drive shaft supported by two or more support elements. The drive shaft is attached to the voice coil and is driven by the voice coil. The impactor assembly further has a load cell attached to a free end of the drive shaft and a biasing device positioned within the magnetic yoke housing.

20 Claims, 15 Drawing Sheets

(56) References Cited

OTHER PUBLICATIONS

Huang, H., et al., Abstract of "A computer-controlled electromechanical hammer to quantify tendon reflex", Engineering in Medicine and Biology Science, 1997, Proceedings of the 19th Annual International Conference of the IEEE, 1997 (2 pages).

Jacobs, K., et al., "An Electro-mechanical Actuator for a Miniature Force Hammer", Conference: 1998 IMAC XVI—16th International Modal Analysis Conference (5 pages).

Norman, P.E., et al., "Development of an Automated Impact Hammer for Modal Analysis of Structures", Australian Government Department of Defence, Defence Science and Technology Organisation, Commonwealth of Australia, Feb. 2012 (33 pages).

The Modal Shop, Inc., Electric Impact Hammer Model 086M92ES, from Internet website at web address <http://www.modalshop.com/excitation/Electric-Impact-Hammer?ID=94>, as of Nov. 29, 2012 (1 page).

Alta Solutions, Inc., AS-1220 Automated Impact Hammer, from Internet website at web address <http://www.altasol.com/products/AS-1220/AS-1220.html>, as of Nov. 29, 2012 (1 page).

European Patent Office Extended European Search Report for Counterpart EP Application No. 13193459, Applicant The Boeing Company, Date of Mailing Mar. 4, 2014, 10 pages.

"The Fundamentals of Modal Testing", Application Note 243-3, Agilent Technologies, May 31, 2000, 56 pages, XP055102951, USA (indicated in European Search Report (see NPL citation 1) as retrieved from the Internet: URL:http://cp.literature.agilent.com/litweb/pdf/5954-7957E.pdf (retrieved on Feb. 18, 2014)), see p. 22.

* cited by examiner

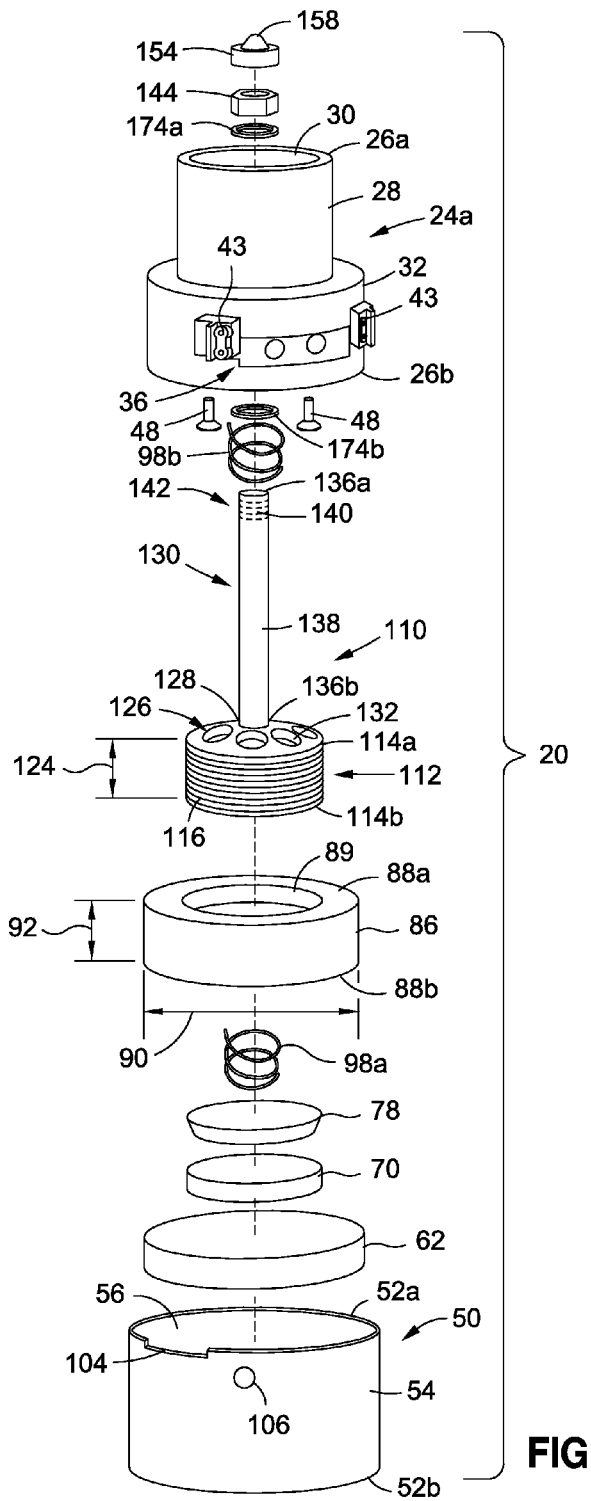
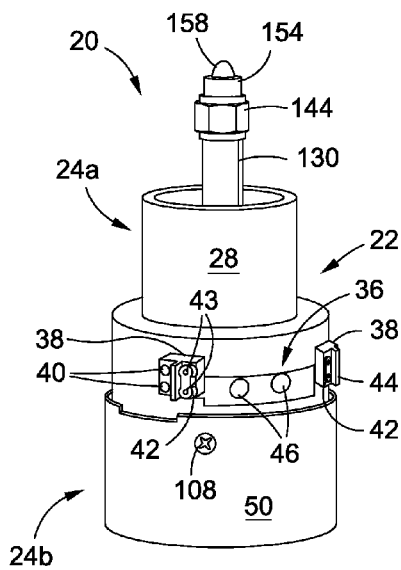
FIG. 2A
FIG. 2B

ELECTRODYNAMIC MODAL TEST IMPACTOR SYSTEM AND METHOD

BACKGROUND

1) Field of the Disclosure

The disclosure relates generally to modal analysis systems and methods, and more particularly, to automated electrodynamic modal test impactor systems and methods.

2) Description of Related Art

Modal analysis is increasingly becoming an important part of the development and testing of structures and component parts in the aerospace, automotive, and structural engineering and design industries, as well as other industries. Modal analysis measures and analyzes the dynamic response of a structure when excited by an input. In structural analysis and testing, modal analysis may be used to determine the natural mode shapes and frequencies of a structure during free vibration. Detailed modal analysis may be needed to assess the potential for structural dynamic problems, such as fatigue, vibration and noise.

Known manual impact excited modal analysis testing methods and systems exist. However, such known manual methods and systems may provide inferior quality data when the impact force produced varies between impacts and/or impact location and the angle of impact varies even slightly during the test. In addition, such known manual methods and systems may have long test times due to increased time between impacts, which may be needed when an operator is trying to control a hammer, and due to increased time from possible double impacts, which may be unacceptable from a data standpoint and may be almost unavoidable with a hammer.

In addition, known automated impact excited modal analysis devices and systems exist. However, such automated devices and systems may be too large to fit in many areas where they would benefit testing, may be unwieldy to handle due to their large size, may contaminate the data by using contact points between the structure being tested and the impact device, and/or may have limited controllability of the impact characteristics. For example, known automated impact excited modal analysis devices, such as instrumented modal test hammers, may provide no ability to reliably control force or impact location or angle of impact. Further, one such known automated impact excited modal analysis device uses a solenoid driven by a specially designed control circuit. However, the use of such solenoid may only be adjusted in amplitude but not pulse width. Moreover, the use of such solenoid may have limited controllability and may distort the response of the structure being tested, such as when it is placed on the structure being tested.

Accordingly, there is a need in the art for an improved electrodynamic modal test impactor system and method that provides advantages over known systems and methods.

SUMMARY

This need for an improved electrodynamic modal test impactor system and method is satisfied. As discussed in the below detailed description, embodiments of the improved electrodynamic modal test impactor system and method may provide significant advantages over existing systems and methods.

In an embodiment of the disclosure, there is provided an electrodynamic modal test impactor system. The system comprises a controller device. The system further comprises an impactor assembly coupled to the controller device. The impactor assembly comprises a housing. The impactor assembly further comprises a permanent magnet positioned within the housing. The impactor assembly further comprises a voice coil positioned within the housing in a magnetic gap of a magnetic yoke housing. The voice coil is driven by the controller device. The impactor assembly further comprises a drive shaft supported by two or more support elements. The drive shaft is attached to the voice coil and is driven by the voice coil. The impactor assembly further comprises a load cell attached to a free end of the drive shaft. The impactor assembly further comprises a biasing device positioned within the magnetic yoke housing.

In another embodiment of the disclosure, there is provided an automated electrodynamic modal test impactor system. The system comprises an audio amplifier. The system further comprises an impactor assembly coupled to the audio amplifier via a plurality of impact signal wires. The impactor assembly comprises a housing comprising a first housing portion and a second housing portion The second housing portion comprises a magnetic yoke housing. The impactor assembly further comprises a magnet assembly housed within the magnetic yoke housing. The magnet assembly comprises a permanent magnet coupled between a magnetic yoke base plate and a magnetic yoke center pole and surrounded by a magnetic yoke outer pole. The impactor assembly further comprises a biasing device positioned within the magnetic yoke housing. The impactor assembly further comprises a voice coil positioned within the housing in a magnetic gap of the magnetic yoke housing. The voice coil is driven by the audio amplifier. The impactor assembly further comprises a drive shaft supported by two or more support elements. The drive shaft is integrally machined to an armature support of the voice coil. The drive shaft is driven by the voice coil. The impactor assembly further comprises a load cell attached to a free end of the drive shaft. The impactor assembly further comprises an impact tip attached to the load cell. The system further comprises an articulating mounting device on which the impactor assembly is mounted. The system further comprise a computer device to review and analyze electrodynamic modal impact test measurements measured with the system.

In another embodiment of the disclosure, there is provided a method of performing electrodynamic modal impact tests. The method comprises the step of imparting short duration force impacts of between about 1 millisecond to about 10 milliseconds in duration on a structure being tested for dynamic modal response. The method further comprises centering a voice coil and a drive shaft driven by the voice coil in a magnetic gap. The method further comprises biasing the voice coil and the drive shaft in a quiescent position to provide a long outward stroke and a minimal inward stroke. The method further comprises measuring an impact force using a load cell attached to a free end of the drive shaft.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein:

FIG. 2A is an illustration of a perspective exploded view of an embodiment of an impactor assembly that may be used in the system and method of the disclosure shown in an unassembled position;

FIG. 2B is an illustration of a perspective view of the impactor assembly of FIG. 2A shown in an assembled position;

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art.

Now referring to the Figures, in one embodiment as disclosed herein, there is provided an electrodynamic modal test impactor system 10 (also referred to herein as "system 10") (see FIG. 9) for performing electrodynamic modal impact tests and testing. As used herein, "electrodynamic modal impact testing" means a form of vibration testing of a structure to be tested where the natural (modal) frequencies, modal masses, modal damping ratios and mode shapes of the structure 197 (see FIG. 9) being tested are determined. In another embodiment as disclosed herein, there is provided a method 300 (see FIG. 15) for performing electrodynamic modal impact tests and testing. Preferably, the system 10 and method 300 are automated.

The teachings of the disclosed embodiments of the system 10 (see FIG. 9) and method 300 (see FIG. 15) may be used to perform electrodynamic modal impact tests and testing on structures and component parts used in the manufacture and production of commercial aircraft, cargo aircraft, military aircraft, rotorcraft, and other types of aircraft or aerial vehicles, as well as aerospace vehicles, satellites, space launch vehicles, rockets, and other aerospace vehicles. It may also be appreciated that disclosed embodiments of the system 10 (see FIG. 9) and method 300 (see FIG. 15) may be used to perform electrodynamic modal impact tests and testing on structures and component parts used in the manufacture and production of automobiles, trucks, buses, ships, boats, trains, or other suitable transport vehicles, as well as architectural structures, such as buildings, towers, bridges, and other types of architectural structures.

Figure 9:
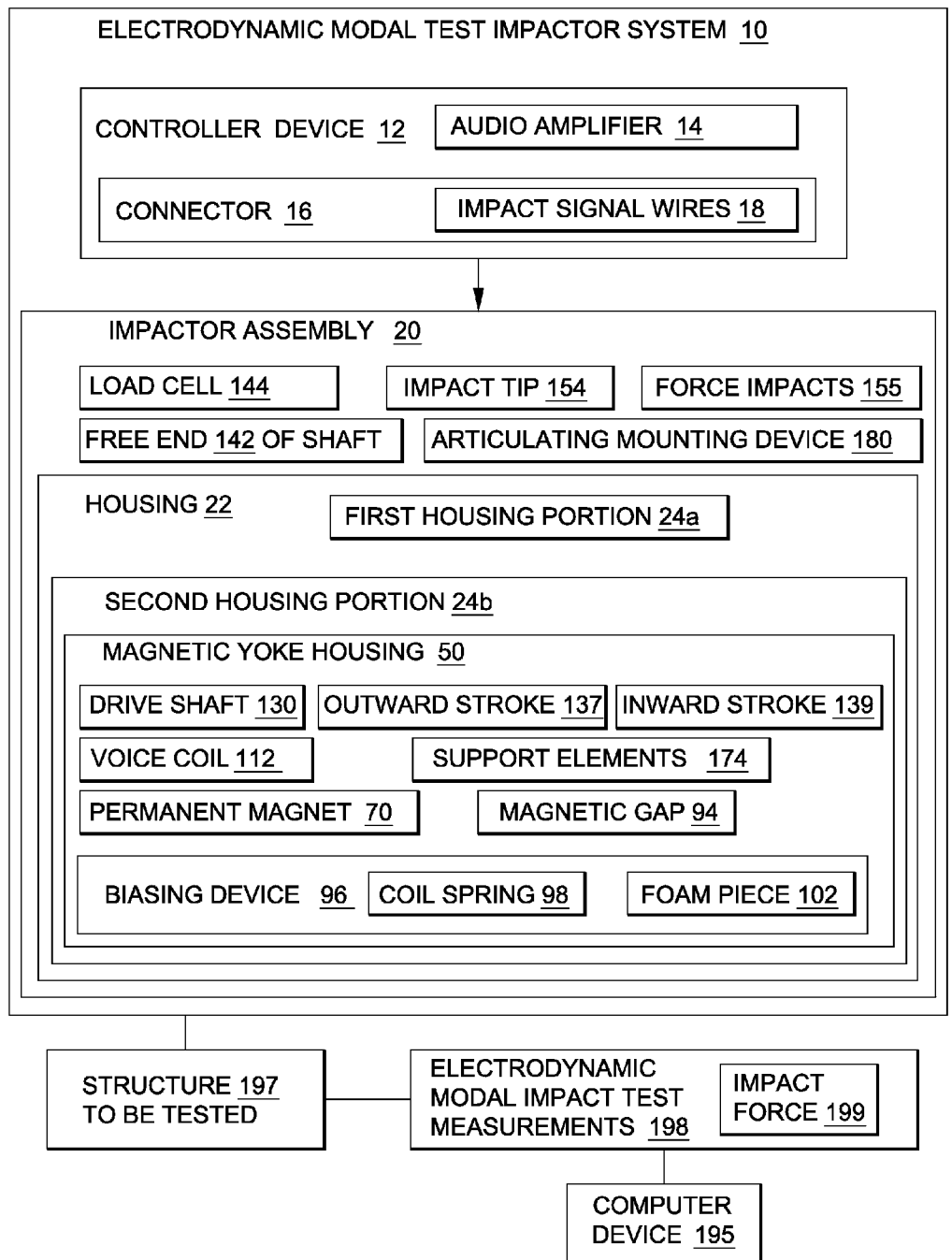
FIG. 9 is an illustration of a block diagram illustrating one of the embodiments of a system of the disclosure.

FIG. 9 is an illustration of a block diagram illustrating one of the embodiments of a system 10 of the disclosure. As shown in FIG. 9, the system 10 comprises controller device 12. The controller device 12 may preferably comprise an audio amplifier 14 (see FIG. 9), such as a high-performance power amplifier optimized for sound, vibration, and electroacoustic applications. Existing Commercial Off the Shelf (COTS) audio amplifiers may be used in the system 10 disclosed herein. As shown in FIG. 9, the system 10 further comprises a connector 16 connected to the controller device 12. The connector 16 may preferably comprise a plurality of impact signal wires 18 (see FIGS. 1B, 9), such as lead wires, or another suitable signal input mechanism as may be appreciated by those skilled in the art.

As shown in FIG. 9, the system 10 further comprises an impactor assembly 20. The impactor assembly 20 is preferably coupled to or connected to the controller device 12 via the connector 16. FIG. 2A is an illustration of a perspective exploded view of an embodiment of the impactor assembly 20 that may be used in the system 10 (see FIG. 9) and method 300 (see FIG. 15) of the disclosure, as shown in an unassembled position. FIG. 2B is an illustration of a perspective view of the impactor assembly 20 of FIG. 2A shown in an assembled position. As shown in FIG. 2B, the impactor assembly 20 comprises a housing 22. As shown in FIGS. 2A-2B, the housing 22 may comprise a first housing portion 24a and a second housing portion 24b. As shown in FIG. 2A, the first housing portion 24a comprises a first end 26a and a second end 26b. As further shown in FIG. 2A, the first housing portion 24a may comprise a cap portion 28 with an opening 30, and a base portion 32 with one or more fastener openings 33 (see FIG. 4) and a base cut-out portion 34 (see FIG. 4). The cap portion 28 and the base portion 32 may be constructed in a unitary configuration or may be separate pieces that may be bonded or attached together with a suitable bonding or attachment means. The second housing portion 24b is configured to slide up and mate with the base portion 32 of the first housing portion 24a when the impactor assembly 20 is assembled for use.

Figure 5:
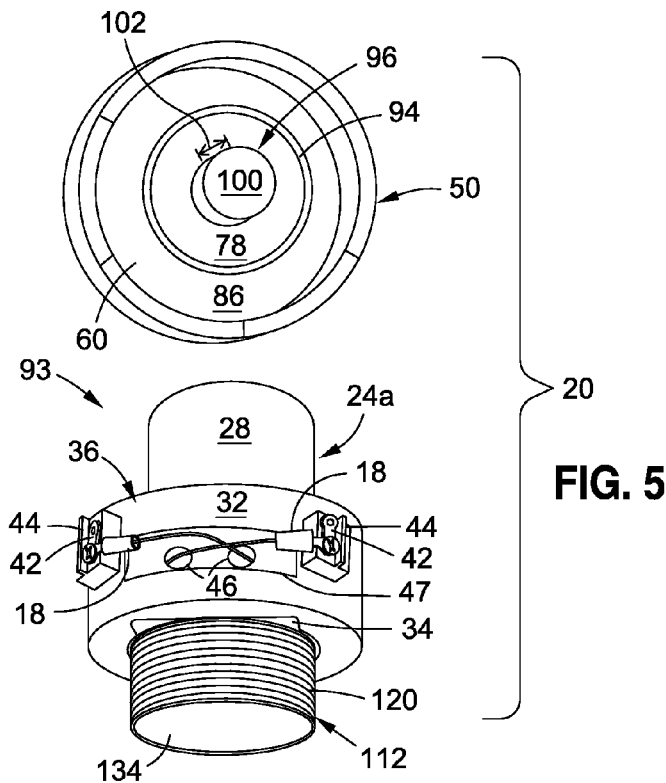
FIG. 5 is an illustration of a perspective view of an embodiment of an impactor assembly with another embodiment of a biasing device that may be used in the system and method of the disclosure shown with the housing portions in a disconnected position.
Figure 6:
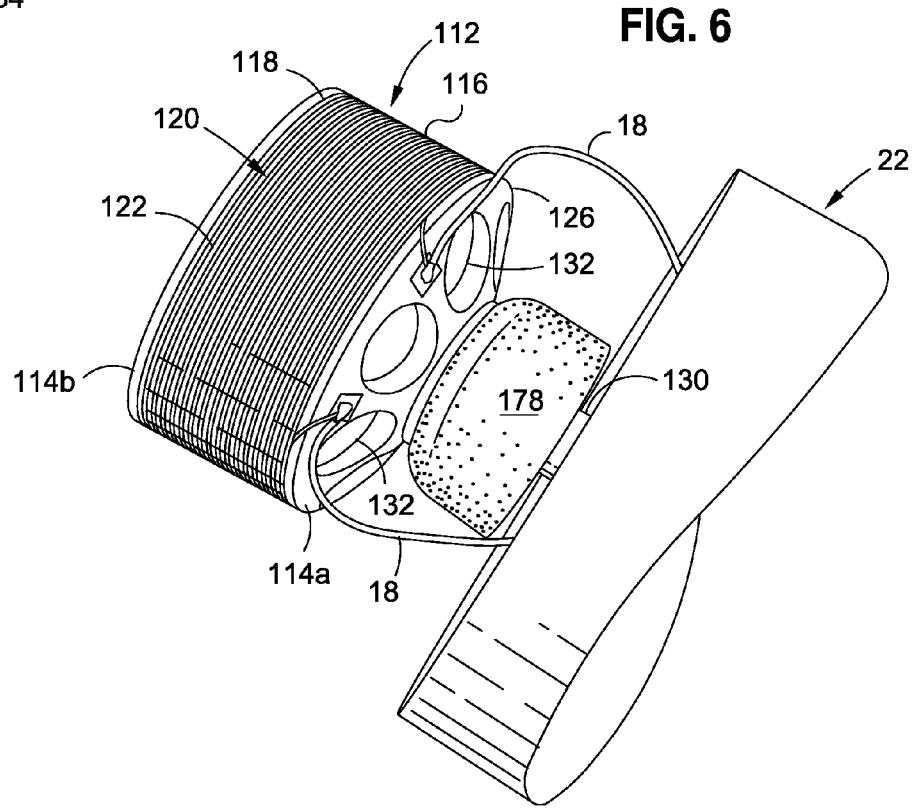
FIG. 6 is an illustration of a close-up perspective view of an embodiment of a voice coil that may be used in the system and method of the disclosure.

As further shown in FIG. 2A, the base portion 32 of the first housing portion 24a may have a controller connector assembly 36 mounted and formed on an exterior 29 of the base portion 32. As shown in FIG. 2A, the controller connector assembly 36 may comprise a pair of input terminals 38 having attachment elements 40 (see FIG. 2B) for attaching the input terminals 38 to the base portion 32. As further shown in FIG. 2A, the controller connector assembly 36 may comprise solder tabs 42 having openings 43 and a bearing surface 44. The impact signal wires 18 may be attached to the solder tabs 42 (see FIGS. 1A and 5). As shown in FIGS. 2A and 6, the controller connector assembly 36 further comprises holes 46 formed through a recessed area 47 on the base portion 32. As further shown in FIG. 2A, the impactor assembly 20 may comprise fasteners 48.

As shown in FIG. 6, the impact signal wires 18 may be routed from the input terminals through the holes 46. The impact signal wires 18 preferably couple signals to the controller device 12, such as in the form of the audio amplifier 14, and the audio amplifier 14 amplifies the low level signals into a high level voltage and current which is preferably passed to a voice coil 112 (see FIG. 2A), discussed in detail below, which cause the voice coil 112 to move, causing an impact tip 154 (see FIG. 2A) to hit or impact—via the drive shaft 130 (see FIG. 2A) and a load cell 144 (see FIG. 2A)—a structure 197 (see FIG. 9) to be tested or under test. The impact signal wires 18 preferably couple the signal from the audio amplifier 14 through the housing 22 to a voice coil 112 (see FIG. 6) in the form of a winding 120 (see FIG. 6).

Figure 4:
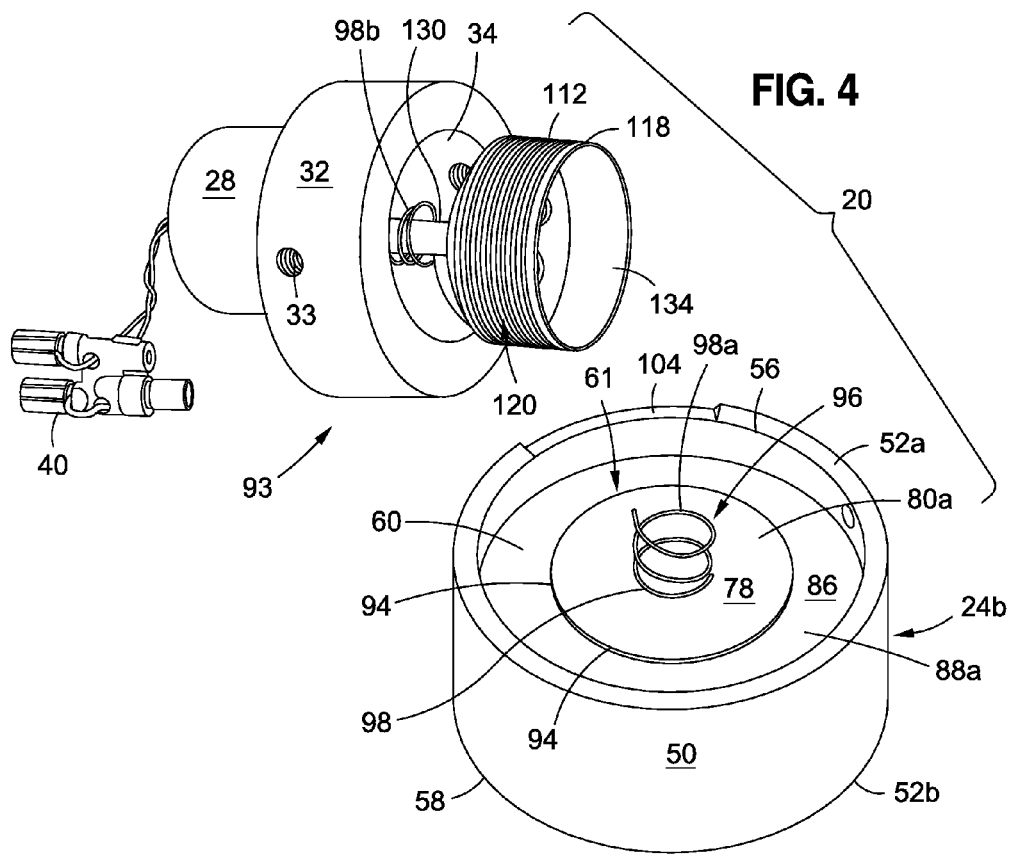
FIG. 4 is an illustration of a perspective view of an embodiment of an impactor assembly with an embodiment of a biasing device that may be used in the system and method of the disclosure shown with the housing portions in a disconnected position.

As further shown in FIG. 2A, the second housing portion 24b may preferably comprise a magnetic yoke housing 50 having a first end 52a, a second end 52b, and a cylindrical body portion 54. The cylindrical body portion 54 may have one or more fastener openings 106 (see FIG. 2A) formed through the body portion 54 for insertion of one or more fasteners 108 (see FIG. 2B). The cylindrical body portion 54 may further have a slotted portion 104 (see FIG. 4) formed on the first end 52a of the magnetic yoke housing 50 for facilitating attachment of the magnetic yoke housing 50 to the first housing portion 24a. The magnetic yoke housing 50 preferably has an open top 56 (see FIG. 2A) and a closed bottom 58 (see FIG. 2A). As shown in FIG. 4, the magnetic yoke housing 50 has an interior 60 for housing a magnet assembly 61 (see also FIG. 3).

Figure 3:
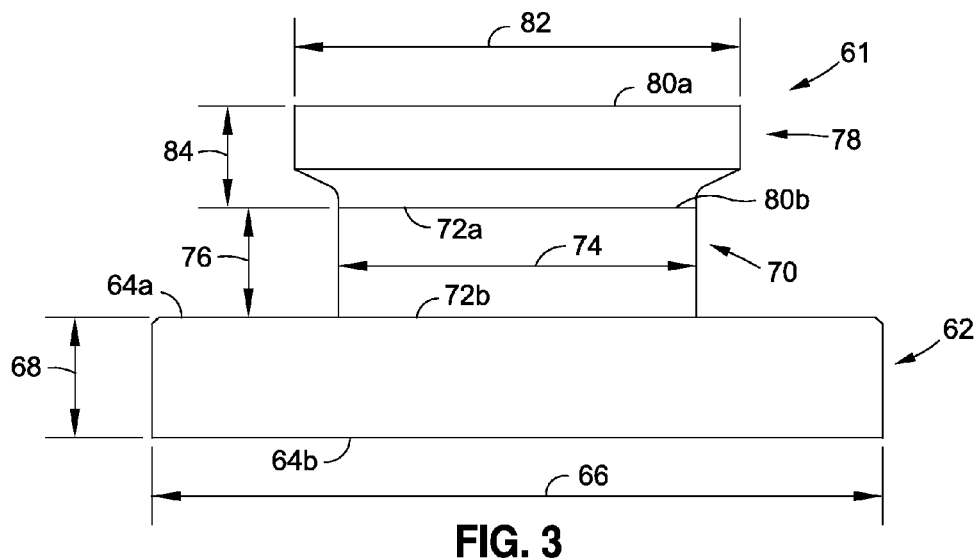
FIG. 3 is an illustration of a close-up front view of an embodiment of a magnet assembly that may be used in the system and method of the disclosure.

FIG. 3 is an illustration of a close-up front view of an embodiment of the magnet assembly 61 that may be used in the system 10 and method 300 of the disclosure. As shown in FIG. 3, the magnet assembly 61 comprises a magnetic yoke base plate 62 (see also FIG. 2A) having a first side 64a, a second side 64b, a diameter 66, and a height 68. When the magnet assembly 61 is inserted into the magnetic yoke housing 50, the second side 64b of the magnetic yoke base plate 62 is adjacent the bottom of the interior 60 of the magnetic yoke housing 50. As further shown in FIG. 3, the magnet assembly 61 comprises a permanent magnet 70 (see also FIG. 2A) having a first side 72a, a second side 72b, a diameter 74, and a height 76. The second side 72b of the permanent magnet 70 is preferably attached or bonded to the first side 64a of the magnetic yoke base plate 62. As further shown in FIG. 3, the magnet assembly 61 comprises a magnetic yoke center pole 78 (see also FIG. 2A) having a first side 80a, a second side 80b, a diameter 82, and a height 84. The second side 80b of the magnetic yoke center pole 78 is preferably attached or bonded to the first side 72a of the permanent magnet 70.

The permanent magnet 70 is thus sandwiched between the magnetic yoke base plate 62 (see FIG. 3) and the magnetic yoke center pole 78 (see FIG. 3). The permanent magnet 70 may comprise Neodymium-Boron-Iron magnets or another suitable magnet. Neodymium-Boron-Iron magnets may be used to provide very high flux densities in a magnetic gap 94 (see FIG. 5) while maintaining a compact design and size. For example, the permanent magnet 70 may have a compact total package size of about 4 inches diameter by 6 inches long. However, other suitable compact sizes may also be used. The permanent magnet 70 may preferably have a flux density of 45 MgO (MegaGauss-Oersteds). The permanent magnet 70 has a north and a south oriented flux path with the north traveling out of the first side 72a of the permanent magnet 70 and through the magnetic yoke center pole 78 and then it turns horizontally and is conducted out to a magnetic yoke outer pole 86 (see FIG. 2A). The magnetic yoke outer pole 86 couples the flux so a circular magnetic path is formed. In another embodiment, the magnet poles may be reversed, such that the flux circulation may also be reversed, since reversal of the polarity of the signal in the voice coil 112 may provide the necessary outward motion of the voice coil 112 and the drive shaft 130.

As further shown in FIG. 2A, the magnet assembly 61 may further comprise the magnetic yoke outer pole 86 having a first side 88a, a second side 88b, a central opening 89, a diameter 90, and a height 92. The magnetic yoke outer pole 86 is preferably inserted into the interior 60 (see FIG. 4) of the magnetic yoke housing 50 with the second side 88b of the magnetic yoke outer pole 86 adjacent the bottom of the interior 60 of the magnetic yoke housing 50. The magnetic yoke outer pole 86 is of a sufficient size and shape so that it fits snugly within the interior 60 of the magnetic yoke housing 50 and houses the magnet assembly 61 within the interior 60 of the magnetic yoke housing 50.

FIG. 4 is an illustration of a perspective view of an embodiment of the impactor assembly 20 with an embodiment of a biasing device 96, comprising a first coil spring 98a and a second coil spring 98b, both working in conjunction and opposition, that may be used in the system 10 and method 300 of the disclosure. FIG. 4 shows the first housing portion 24a and the second housing portion 24b in a disconnected position 93. As shown in FIG. 4, when the second housing portion 24b is assembled, the magnetic yoke outer pole 86 sits on the magnetic yoke base plate 62, and surrounds the permanent magnet 70, and the magnetic yoke center pole 78 of the magnetic assembly 61. Preferably, the first side 88a of the magnetic yoke outer pole 86 is flush with the first side 80a of the magnetic yoke center pole 78. As shown in FIG. 4, a magnetic gap 94 or space is formed between the magnetic yoke outer pole 86 and the magnetic yoke center pole 78. The magnetic gap 94 may preferably have a height of about 0.25 inch to about 0.5 inch, and the voice coil 112 (see FIG. 6)

preferably has a height of about 1 inch to about 1.2 inches. Preferably, the voice coil 112 is positioned in the magnetic gap 94 even if the voice coil 112 is moving. The system 10 and method 300 disclosed herein have optimized the height of the voice coil 112 in relation to the height and size of the magnetic gap 94. As shown in FIG. 4, the biasing device 96 comprising the first coil spring 98a is preferably attached to the first end 80a of the magnetic yoke center pole 78, and the opposing biasing device 96, comprising the second coil spring 98b, is preferably attached to the inner face of the first housing portion 24a. In one embodiment, the biasing device 96 may comprise a coil spring 98 (see FIG. 4). In another embodiment, the biasing device 96 may comprise a foam piece 100 (see FIG. 5). FIG. 5 is an illustration of a perspective view of an embodiment of the impactor assembly 20 with another embodiment of the biasing device 96, such as in the form of first coil spring 98a and second coil spring 98b, that may be used in the system 10 and method 300 of the disclosure. FIG. 5 shows the first housing portion 24a and the second housing portion 24b in a disconnected position 93. Preferably, the biasing device 96 has a height 102 (see FIG. 5) that projects upwardly from the magnetic yoke center pole 78 a sufficient and desired distance from the magnetic yoke center pole 78. The biasing device 96 is preferably used to position a voice coil 112 (see FIG. 5) in the magnetic gap 94 (see FIG. 5) and to return an armature support 126 (see FIG. 6) to that same position after each impact is performed.

As shown in FIG. 2A, the impact assembly 20 further comprises a voice coil drive shaft assembly 110. The voice coil drive shaft assembly 110 comprises a voice coil 112 (see FIGS. 2A and 6) with an armature support 126 (see FIGS. 2A and 6) and a drive shaft 130 (see FIG. 2A). The drive shaft 130 is preferably integrally machined with the armature support 126 and the voice coil 112, thus eliminating parts and providing structural integrity. FIG. 6 is an illustration of a close-up perspective view of an embodiment of the voice coil 112 that may be used in the system 10 and method 300 of the disclosure. As shown in FIGS. 2A and 6, the voice coil 112 is preferably in the form of a winding 120 (see FIG. 6). The winding 120 preferably comprises a wire 122 (see FIG. 6) that is preferably very thin and that is wound around and bonded or attached to the exterior 118 (see FIG. 6) of an armature support 126 (see FIG. 6). The wire 122 preferably has a gauge measurement of 30 gauge or greater (i.e., smaller wire diameter, the larger the number, the smaller the gauge), with 30 gauge being more preferred. The impactor assembly 20 is preferably designed as a low duty cycle impactor, so it may use the gauge wires 122 which would otherwise be damaged by a continuous current flow at the levels intended during testing. For example, because the impactor assembly 20 would be a low duty cycle impactor, it would have voltage through it less than 1% of the time, and thus more current may be carried through the impactor assembly 20 which in other circumstances could melt the gauge wires 122 of the winding 120. Preferably, a range of current that the impact assembly 20 may handle may be from about 0.1 amps to about 10 amps. As shown in FIG. 2A, the voice coil 112 has a height 124. The winding 120 may be attached to the voice coil 112 via an adhesive material such as glue or another suitable adhesive. The voice coil 112 is driven by the controller device 12 (see FIG. 9), such as in the form of the audio amplifier 14 (see FIG. 9).

As shown in FIGS. 2A and 6, the voice coil drive shaft assembly 110 further comprises an armature support 126 having a first end 114a, a second end 114b, a body portion 116, an exterior 118 (see FIG. 6), and an interior 134 (see FIG. 5). As shown in FIG. 6, the voice coil 112 in the form of the winding 120 is preferably wound around and bonded to the exterior 118 of the armature support 126. The second end 114b (see FIG. 2A) of the armature support 126 (see FIG. 2A) is preferably of a suitable size and shape to enable it to fit within the magnetic yoke housing 50 (see FIG. 5). The voice coil 112 and the armature support 126 are preferably formed as a unitary piece. However, the voice coil 112 and the armature support 126 may also be separate pieces that may be attached or bonded together. In this embodiment, the armature support 126 has a central opening 128 (see FIG. 2A) for insertion of the drive shaft 130. The armature support 126 further has a plurality of openings 132 (see FIGS. 2A, 6) that reduce the weight of the moving armature support 126 and the drive shaft 130 and permit air to pass from one side of the armature support 126 to the other side as it moves, thus eliminating any trapped air mass.

The voice coil drive shaft assembly 110 further comprises the drive shaft 130 (see FIG. 2A) that is preferably integrally machined with the armature support 126 (see FIG. 2A). As shown in FIG. 2A, the drive shaft 130 comprises a first end 136a, a second end 136b, and an elongated body portion 138. As shown in FIG. 2A, the second end 136b of the drive shaft 130 is inserted into the central opening 128 (see FIG. 2A) of the armature support 126 (see FIG. 2A). As further shown in FIG. 2A, the first end 136a is preferably a free end 142 for connection to a load cell 144 (see FIGS. 2A, 7A) or for direct connection to an impact tip 154 (see FIG. 7B). As shown in FIG. 2A, the first end 136a may have a threaded interior portion 140 for forming a threaded connection to the load cell 144 (see FIGS. 2A, 7A) or for forming a threaded connection to the impact tip 154 (see FIG. 7B).

Figure 8A:
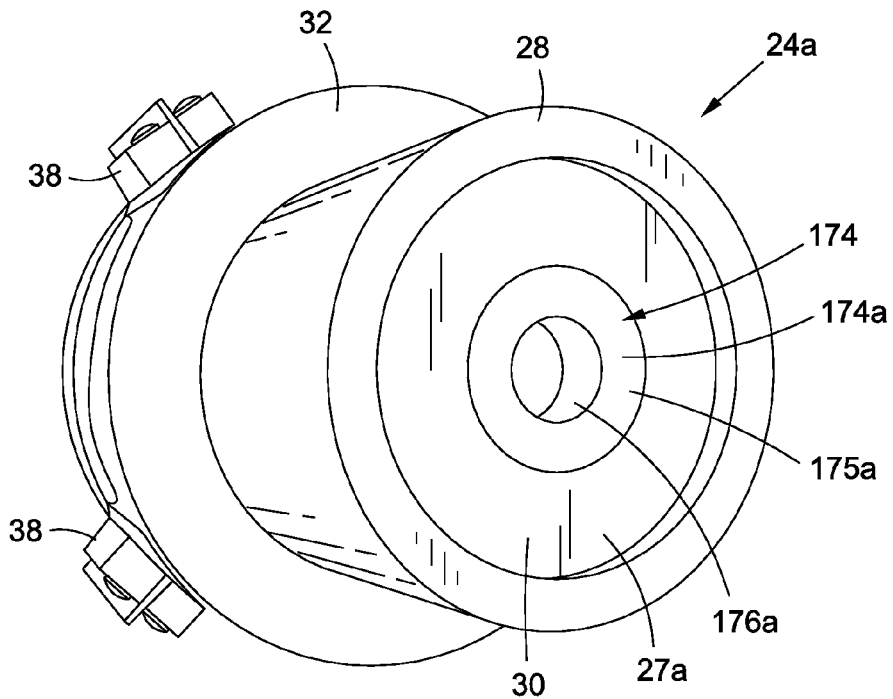
FIG. 8A is an illustration of a top perspective view of the interior of the first housing portion showing a first end plate with a first support element such as a bushing.
Figure 8B:
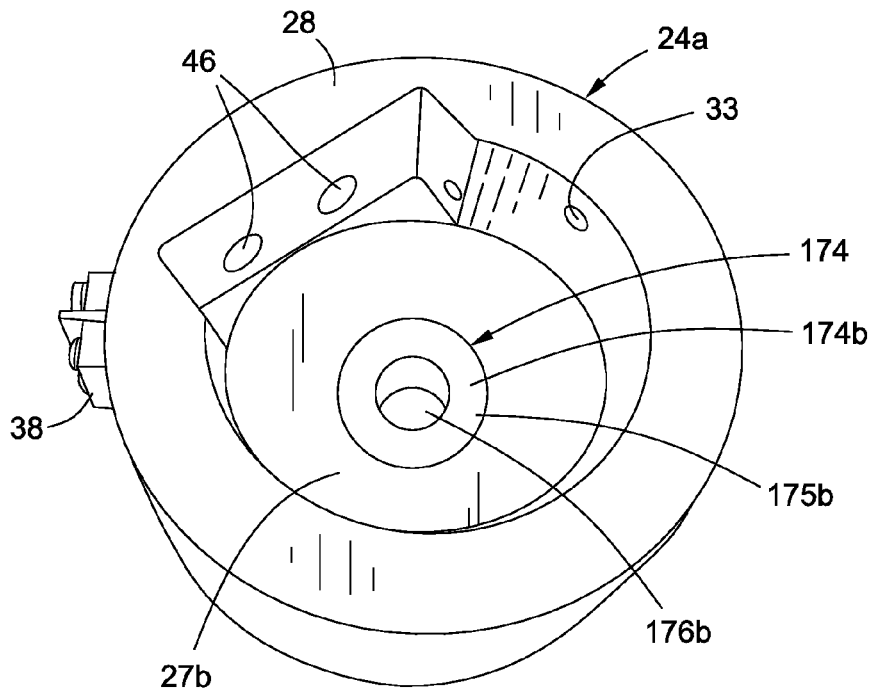
FIG. 8B is an illustration of a top perspective view of the interior of the first housing portion showing a second end plate with a second support element such as a bushing.

The drive shaft 130 is preferably supported by two or more support elements 174 (see FIGS. 2A, 8A-8B), including a first support element 174a (see FIG. 8A), such as in the form of a bushing 175a, and including a second support element 174b (see FIG. 8B), such as in the form of a bushing 175b. FIG. 8A is an illustration of a top perspective view of the interior 30 of the cap portion 28 of the first housing portion 24a showing a first end plate 27a with the first support element 174a, such as in the form of bushing 175a. FIG. 8A also shows the base portion 32 and the input terminal stops 38. FIG. 8B is an illustration of a top perspective view of the interior 30 of the cap portion 28 of the first housing portion 24a showing a second end plate 27b with a second support element 174b, such as in the form of busing 175b. FIG. 8B also shows the fastener opening 33, holes 46, and input terminal strip 38. The support elements 174 may also comprise linear recirculating ball bushings (not shown) or another suitable support element appreciated by those skilled in the art.

The support elements 174, including the first support element 174a (see FIG. 8A), such as in the form of bushing 175a, and including the second support element 174b (see FIG. 8B), such as in the form of bushing 175b, help facilitate long outward strokes 137 (see FIG. 9) of the voice coil 112 and drive shaft 130, which may help prevent multiple impacts (i.e. no flexures constraining axial motion). The support elements 174 (see FIGS. 8A-8B), such as in the form of first support element 174a (see FIG. 8A), such as comprising bushing 175a (see FIG. 8A), and second support element 174b (see FIG. 8B), such as comprising bushing 175b (see FIG. 8B), are preferably aluminum machined parts machined to match the diameter of the drive shaft 130. The support elements 174, such as in the form of first support element 174a and second support element 174b (see FIG. 2A) guide the drive shaft 130 to provide frictionless mounting and to minimize or eliminate any side to side movement of the drive shaft 130.

The drive shaft 130 is preferably driven by the voice coil 112. As shown in FIG. 4, the second coil spring 98b may be positioned around the drive shaft 130 between the housing 22 and the armature support 126. The armature support 126 may assist in biasing the voice coil 112 to a desired position and may pre-compress the first coil spring 98a and the second coil spring 98b, so that the first coil spring 98a and the second coil spring 98b do not go to a completely relaxed position during movement of the voice coil 112. The first coil spring 98a and the second coil spring 98b preferably work in opposition to each other in order to hold the voice coil 112 in the desired neutral position and to help return the voice coil 112 to that position after the impact has been completed. Another suitable embodiment may include using cantilever springs (not shown), such as single leaf cantilever springs or leaf springs, in place of the first coil spring 98a and the second coil spring 98b.

Alternatively, the biasing device 96 may comprise a first foam piece 100 (see FIG. 5) and a second foam piece 178 (see FIG. 6). The first foam piece 100 (see FIG. 5) may be positioned between the armature support 126 and the magnetic yoke center pole 78, and the second foam piece 178 (see FIG. 6) may be positioned around the drive shaft 130 between the housing 22 and the armature support 126 and voice coil 112. The biasing device 96, such as in the form of shaft foam ring 178 and foam piece 100, also preferably work in opposition to each other in order to hold the voice coil 112 in the desired neutral position and to help return the voice coil 112 to that position after the impact has been completed. The foam material comprising first foam piece 100 and the second foam piece 178 may preferably reduce the tendency of the voice coil 112 to oscillate after the impact is completed.

Figure 7A:
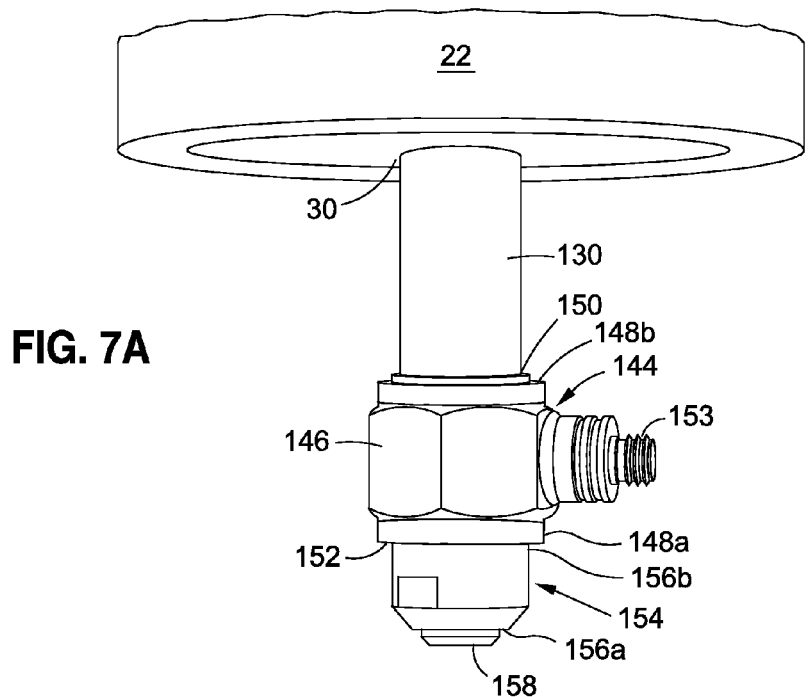
FIG. 7A is an illustration of a side perspective view of an embodiment of an impact tip, load cell, and drive shaft connection that may be used in the system and method of the disclosure.

As shown in FIG. 2A and FIG. 7A, the impactor assembly 20 may further comprise a load cell 144. The load cell 144 may comprise a suitable Commercial Off The Shelf (COTS) load cell 146. FIG. 7A is an illustration of a side perspective view of an embodiment of an impact tip 154 and a drive shaft 130 connection with the load cell 144 connected therebetween that may be used in the system 10 and method 300 of the disclosure. As shown in FIG. 7A, the load cell 144 may comprise a first end 148a, a second end 148b, a shaft attach opening 150 for attachment to the drive shaft 130, an impact tip attach opening 152 for attachment to the impact tip 154, and a signal connector portion 153.

Figure 7B:
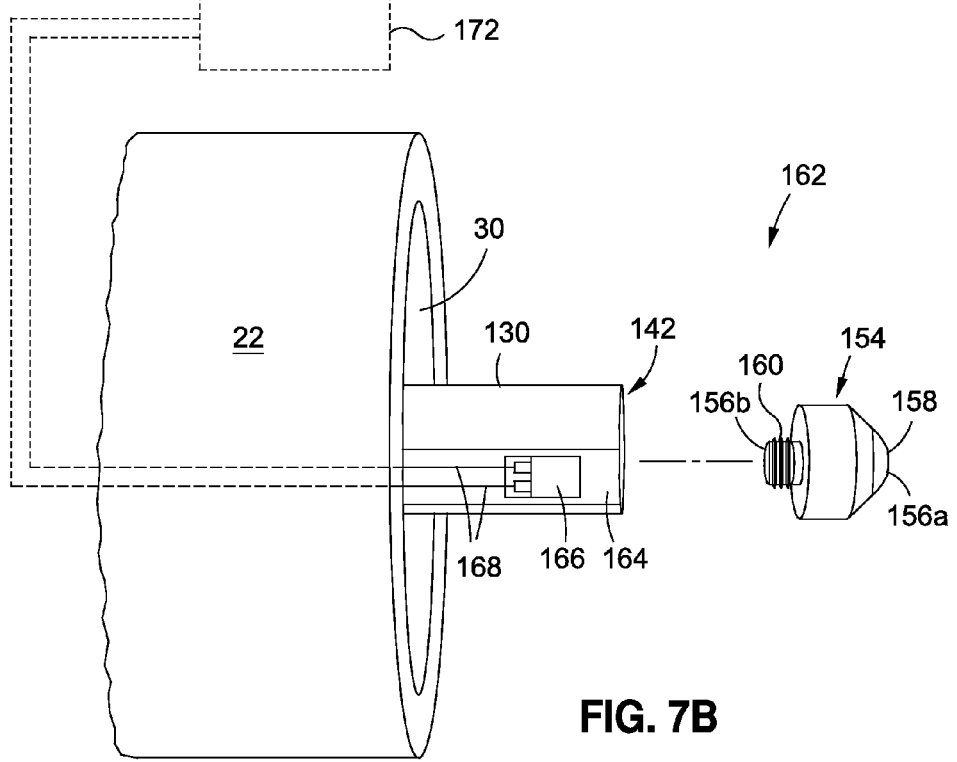
FIG. 7B is an illustration of a side perspective view of another embodiment of an impact tip and drive shaft with strain gauges connected that may be used in the system and method of the disclosure.

As shown in FIG. 2A and FIGS. 7A-7B, the impactor assembly 20 may further comprise an impact tip 154. As shown in FIGS. 7A-7B, the impact tip 154 may comprise a first end 156a having a tip portion 158 and may further comprise a second end 156b having a threaded connector portion 160 (see FIG. 7B). For embodiments of the impactor assembly 20 used herein in electrodynamic modal impact testing, the tip portions 158 may have various materials as the actual impact surface, to allow the softness or hardness of the tip portion 158 to be changed, if desired. For example, the tip portion 158 may comprise a rubber tip, a steel tip, a plastic tip, or another suitable tip material. As shown in FIG. 7A, the impact tip 154 is connected to the load cell 144.

In another embodiment, as shown in FIG. 7B, the load cell 144 between the drive shaft 130 and the impact tip 154 may be removed, and the impact tip 154 may be connected directly to the drive shaft 130. FIG. 7B is an illustration of a side perspective view of another embodiment of the impact tip 154 and the drive shaft 130 connection with the load cell 144 removed that may be used in the system 10 and method 300 of the disclosure. In this embodiment, as shown in FIG. 7B, the impact tip 154 and drive shaft 130 may be in the form of an integral force measuring device 162 where the drive shaft 130 may have one or more flat sides 164 (see FIG. 7B) to which one or more strain gauges 166 may be attached or embedded. The strain gauge 166, as shown in FIG. 7B, may be mated with another strain gauge (not shown) on the opposite side of the drive shaft 130 and may be electrically connected with a suitable electrical connection (not shown) that may provide a signal proportional to the force applied to the drive shaft 130 by the impact. Strain gauge wires 168 (see FIG. 7B) that are preferably very thin may be attached to the strain gauges 166 and may be routed down (attached via an adhesive such as glue) the one or more flat sides 164 of the drive shaft 130 to a terminal strip (not shown) that may be located on the armature support 126 (see FIG. 6), similar to how the impact signal wires 18 to the voice coil 112 may be routed. The strain gauge wires 168 may be fed out through the holes 46 (see FIG. 2B) in the housing 22 (see FIG. 2B) that the impact signal wires 18 (see FIG. 5) may be routed through, to suitable signal conditioners 172 (see FIG. 7A) that may provide a high level voltage proportional to force that may be measured during the electrodynamic modal impact testing. Such an embodiment may reduce the weight of the voice coil 112 that is moving and the drive shaft 130 may enhance the performance of the integral force measuring device 162.

As shown in FIG. 9, the system 10 may further comprise an articulating mounting device 180 to mount the impactor assembly 20 on during electrodynamic modal impact testing. A suitable articulating mounting device 180 may be obtained from Panavise Products, Inc. of Reno, Nev. However, other suitable Commercial Off The Shelf (COTS) articulating mounting devices that provide similar articulation and positioning of the impactor assembly 20 may also be used.

The design of the impactor assembly 20 preferably allows the impactor assembly 20 to be supported directly on the small, articulating mounting device 180 that will provide complete freedom of position and orientation of the impactor assembly 20 with respect to the structure 197 (see FIG. 9) to be tested or being tested. The articulating mounting device 180 may provide three (3) degrees of freedom of rotation. Three (3) degrees of freedom in translation may be provided by any support structure (not shown) that the articulating mounting device 180 is supported on or attached to, such as a table (not shown) that the articulating mounting device 180 may be clamped to, a tripod (not shown) that the articulating mounting device 180 may be mounted on, a step of a ladder (not shown) that the articulating mounting device 180 may be attached to, a hand rail of a hydraulic lift (not shown) or an extendable pole set-up (not shown) that uses sliding tube clamps that the articulating mounting device 180 may be attached to, or another suitable support structure.

Figure 1A:
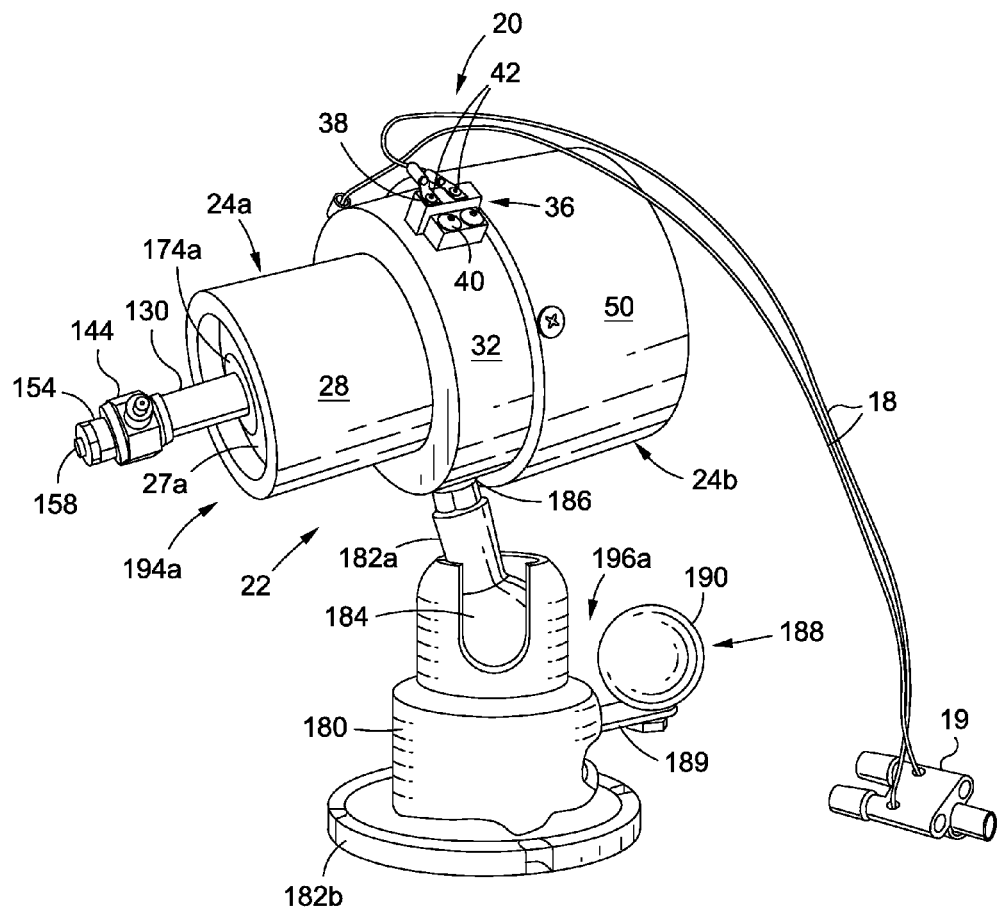
FIG. 1A is an illustration of a perspective view of an embodiment of an impactor assembly that may be used in the system and method of the disclosure shown mounted on an articulating mounting device in a first position.

FIG. 1A is an illustration of a perspective view of an impactor assembly 20 that may be used in the system 10 and method 300 of the disclosure. The impactor assembly 20 is shown in FIG. 1A fully assembled and mounted on an embodiment of the articulating mounting device 180. FIG. 1A shows the impactor assembly 20 with the housing 22 comprising the first housing portion 24a and the second housing portion 24b. FIG. 1A further shows the cap portion 28 of the first housing portion 24a where the cap portion 28 has a first support element 174a. FIG. 1A further shows the base portion 32 of the first housing portion 24a and the magnetic yoke housing 50. FIG. 1A further shows one embodiment of the controller connector assembly 36 mounted on the base portion 32 of the first housing portion 24a. The controller connector assembly 36 shows the attachment elements 40 and the solder tabs 42 connected to the input terminal strip 38. The impact signal wires 18 are connected to the input terminal strip 38 at one end and have an end connector portion 19 at the other end that may be connected to the controller device 12 (see FIG. 9), such as in the form of the audio amplifier 14 (see FIG. 9). FIG. 1A further shows the drive shaft 130 connected to the load cell 144 which is connected to the impact tip 154 having the tip portion 158.

As shown in FIG. 1A, the articulating mounting device 180 may comprise a first attachment end 182a, a second support base end 182b, an articulating portion 184 for articulating the impactor assembly 20, and an attachment portion 186 for attaching the impactor assembly 20 to the articulating mounting device 180. The articulating mounting device 180 further comprises a positioning handle 189 and a loosening and tightening element 190. The second support base end 182b may allow articulation or movement of the impactor assembly 20 by loosening the handle 189 with the loosening and tightening element 190 and moving the impactor assembly 20 to the desired angle or position, then re-tightening a clamping device 192 (see FIG. 1C) by moving the positioning handle 189 back to a locked position 188 (see FIGS. 1A-1C). As shown in FIG. 1A, the impactor assembly 20 is shown in a forward tilt position 194a and the articulating portion 184 is in a first position 196a.

Figure 1B:
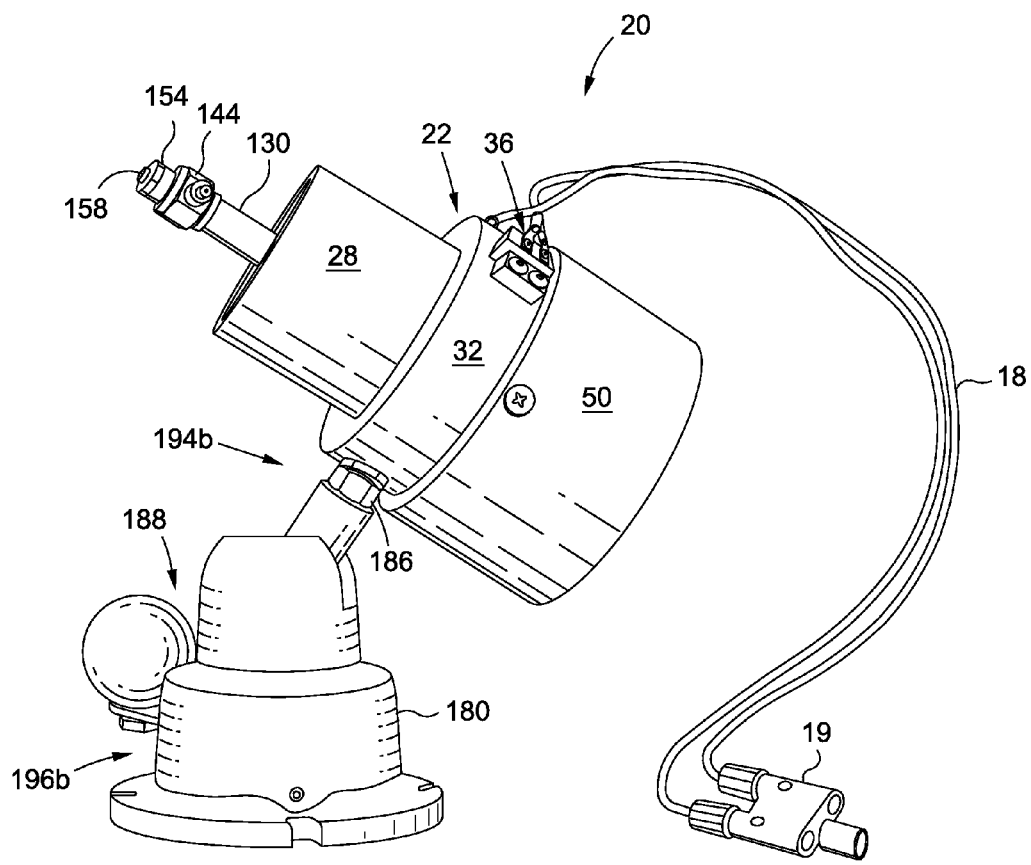
FIG. 1B is an illustration of a perspective view of the impactor assembly of FIG. 1A mounted on the articulating mounting device in a second position.
Figure 1C:
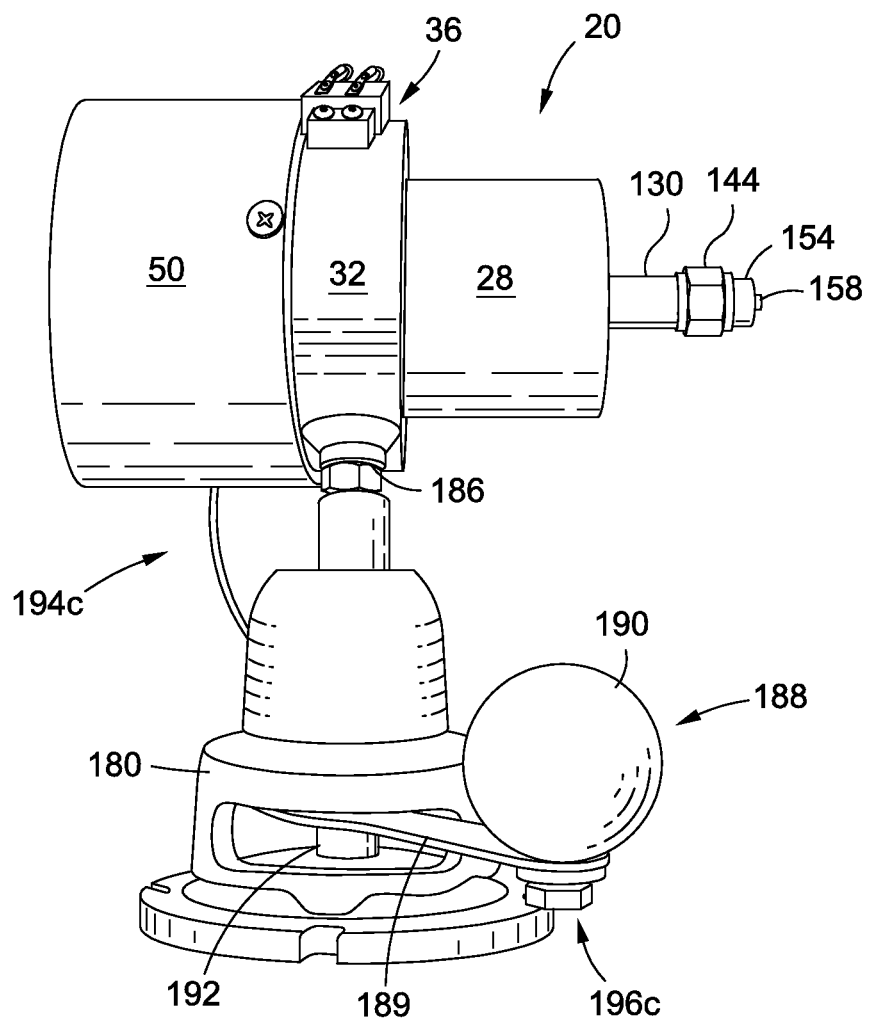
FIG. 1C is an illustration of a perspective view of the impactor assembly of FIG. 1A mounted on the articulating mounting device in a third position.

FIG. 1B is an illustration of a perspective view of the impactor assembly 20 of FIG. 1A shown mounted on the articulating mounting device 180. As shown in FIG. 1B, the impactor assembly 20 is shown in a backward tilt position 194b and the articulating portion 184 is in a second position 196b. FIG. 1C is an illustration of a perspective view of the impactor assembly 20 of FIG. 1A shown mounted on the articulating mounting device 180. As shown in FIG. 1C, the impactor assembly 20 is shown in a rotated position 194c and the articulating portion 184 is in a third position 196c.

In an embodiment of the disclosure, there is provided an automated electrodynamic modal test impactor system 10 (see FIG. 9). The system 10 comprises an audio amplifier 14 (see FIG. 9). The system 10 further comprises an impactor assembly 20 (see FIG. 2A) coupled to the audio amplifier 14 via a plurality of impact signal wires 18 (see FIG. 1A). The impactor assembly 20 comprises a housing 22 comprising a first housing portion 24a (see FIG. 1A) and a second housing portion 24b (see FIG. 1A). The first housing portion 24a may comprise a cap portion 28 (see FIG. 1A) and a base portion 32 (see FIG. 1A). The second housing portion 24b comprises a magnetic yoke housing 50 (see FIG. 2A). The impactor assembly 20 further comprises a magnet assembly 61 (see FIG. 3) housed within the magnetic yoke housing 50. The magnet assembly 61 comprises a permanent magnet 70 (see FIG. 3) coupled between a magnetic yoke base plate 62 (see FIG. 3) and a magnetic yoke center pole 78 (see FIG. 3) and surrounded by a magnetic yoke outer pole 86 (see FIG. 3). The permanent magnet 70 may comprise a Neodymium-Boron-Iron magnet having a compact size of about 2 inches diameter by 0.5 inches long. The impactor assembly 20 further comprises embodiments of a biasing device 96 (see FIGS. 4, 5, 6) comprising a first coil spring 98a (see FIG. 4) or a first foam piece 100 (see FIG. 5) positioned within the magnetic yoke housing 50, working in conjunction with a second coil spring 98b (see FIG. 4) or a second foam piece 178 (see FIG. 6), respectively, between the armature support 126 and the magnetic yoke center pole 78.

The impactor assembly 20 further comprises a voice coil 112 (see FIG. 2A) positioned within the housing 22 in a magnetic gap 94 (see FIG. 5) of the magnetic yoke housing 50. The voice coil 112 is preferably driven by the audio amplifier 14. The voice coil 112 is preferably in the form of a winding 120 (see FIG. 6) comprising a gauge wires 122 (see FIG. 6) wound around and bonded to an exterior 118 of the armature support 126. The gauge wire 122 preferably has a gauge measurement of 30 gauge or greater. The impactor assembly 20 further comprises a drive shaft 130 (see FIG. 2A) supported by two or more support elements 175 (see FIGS. 8A-8B). The support elements 174 (see FIGS. 2A, 8A-8B) preferably comprise first support element 174a, such as in the form of bushing 175a, and second support element 174b, such as in the form of bushing 175b. The first support element 174a may have an opening 176a (see FIG. 8A), and the second support element 174b may have an opening 176b (see FIG. 8B). The diameter of the opening 176a (see FIG. 8A) and the diameter of the opening 176b (see FIG. 8B) preferably correspond to an outer diameter of the drive shaft 130 such that the support elements 174 guide the drive shaft 130 through the opening 176a (see FIG. 8A) and the opening 176b (see FIG. 8B). The drive shaft 130 is preferably integrally machined to the armature support 126 (see FIG. 2A) of the voice coil drive shaft assembly 110. The drive shaft 130 is preferably driven by the voice coil 112. The impactor assembly 20 further comprises a load cell 144 (see FIG. 2A) attached to a free end 142 (see FIG. 2A) of the drive shaft 130. The impactor assembly 20 further comprises an impact tip 154 (see FIG. 2A) attached to the load cell 144. The system 10 may further comprise an integral force measuring device 162 (see FIG. 7B) comprising one or more strain gauges 166 (see FIG. 7B) and one or more strain gauge wires 168 (see FIG. 7B) attached to the drive shaft 130 that may be used in place of the load cell 144, and the impact tip 154 (see FIG. 7B) is attached directly to the free end 142 of the drive shaft 130.

The system 10 further comprises an articulating mounting device 180 (see FIG. 1A) on which the impactor assembly 10 may be mounted. The system 10 further comprises a computer device 195 (see FIG. 9) such as a computer device and processor unit, to review and analyze electrodynamic modal impact test measurements 198 (see FIG. 9) measured with the system 10.

As discussed, in part, above, FIG. 9 is an illustration of a block diagram illustrating one of the embodiments of an electrodynamic modal test impactor system 10 of the disclosure. As shown in FIG. 9, the system 10 comprises the controller device 12, such as in the form of audio amplifier 14, a connector 16 such as in the form of impact signal wires 18, and an impact assembly 20 connected to the controller device 12 via the connector. As further shown in FIG. 9, the impactor assembly 20 comprises a housing 22 with a first housing portion 24a and a second housing portion 24b. The second housing portion 24b comprises a magnetic yoke housing 50 having a permanent magnet 70 with a biasing device 96 that may be in the form of a first coil spring 98a and a second coil spring 98b (see FIG. 2A) or in the form of a first foam piece 100 (see FIG. 5) and a second foam piece 178 (see FIG. 6). The voice coil 112 preferably is in the form of a winding 120 that fits within the magnetic gap 94 and is attached to or integral with the drive shaft 130. The drive shaft 130 is preferably supported with support elements 174 (see FIGS. 8A-8B), preferably comprising first support element 174a, such as in the form of bushing 175a, and second support element 174b, such as in the form of bushing 175b, allowing long outward strokes 137 and minimal inward strokes 139 of the voice coil 112 and the drive shaft 130. As shown in FIG. 9, the impactor assembly 20 further includes a load cell 144 attached to the free end 142 of the drive shaft 130, and the impact tip 154 that imparts force impacts 155 on the structure 197 to be tested in order to take electrodynamic modal impact test measurements 198. As further shown in FIG. 9, the impactor assembly may be mounted on an articulating mounting device 180. The system 10 may further comprise a computer device and/or processor unit to review and analyze the test data. The computer device 195 may use known modal analysis software for further analyzing the test data and generating and displaying the mode shapes in animation or graphics.

Figure 15:
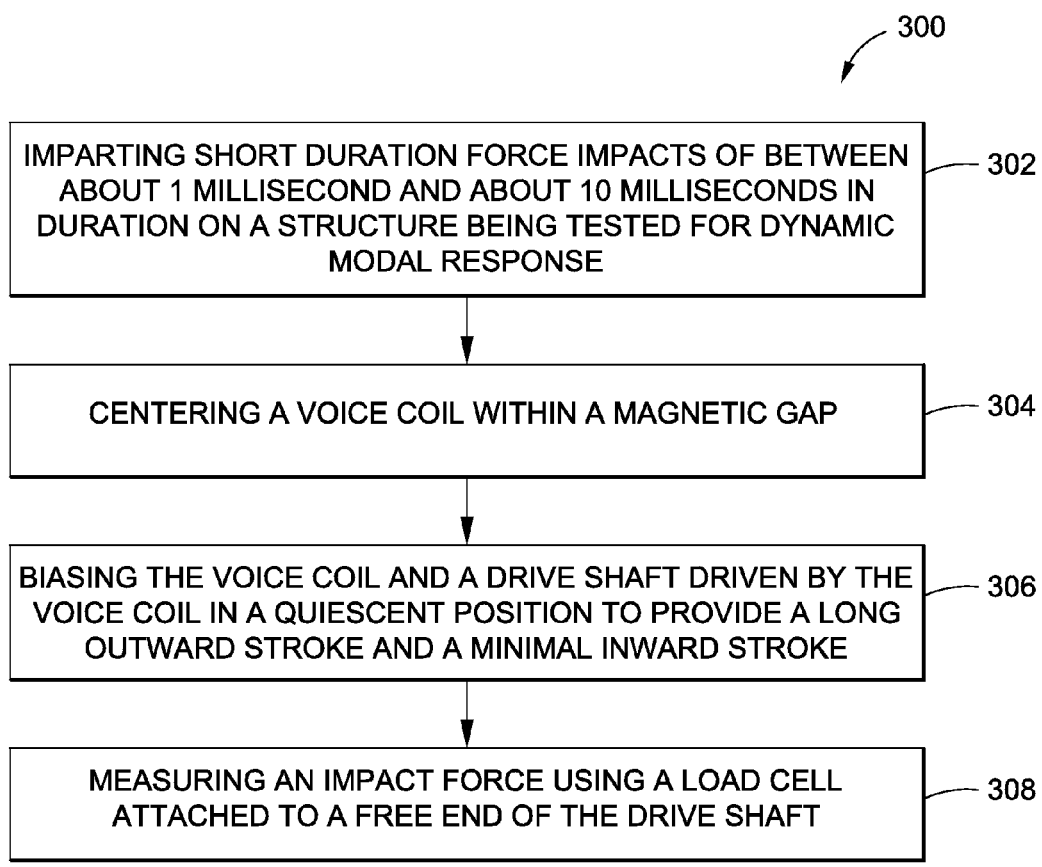

In one embodiment of the disclosure, there is also provided a method 300 of performing electrodynamic modal impact tests. FIG. 15 is an illustration of a flow diagram illustrating one of the embodiments of the method 300 of the disclosure. As shown in FIG. 15, the method 300 comprises the step 302 of imparting short duration force impacts 155 (see FIG. 9) of between about 1 millisecond to about 10 milliseconds in duration on the structure 197 (see FIG. 9) being tested for dynamic modal response. Preferably, the structure 197 being tested is excited with force inputs that contain energy distributed across the frequency band expected when the structure is in service or operation.

As further shown in FIG. 15, the method 300 comprises the step 304 of centering the voice coil 112 (see FIG. 6), such as in the form of the winding 120 (see FIG. 6), within a magnetic gap (94) (see FIG. 5). The centering may be accomplished via the precise manufacturing and assembly of the impactor assembly 20. In particular, the centering of the voice coil 112, such as in the form of winding 120, in the magnetic gap 94 may be accomplished by precisely machining the bushings 175a, 175b (see FIGS. 8A-8B), the housing 22 (see FIG. 2A), the magnetic yoke base plate 62 (see FIG. 2A), the magnetic yoke center pole 78 (see FIG. 2A), and the magnetic yoke outer pole 86 (see FIG. 2A), so that when assembled, the voice coil 112, such as in the form of winding 120, is centered in the magnetic gap 94.

As further shown in FIG. 15, the method 300 comprises the step 306 of biasing the voice coil 112 (see FIG. 6) and a drive shaft 130 driven by the voice coil 112, in a desired quiescent position (i.e., non-moving, still, inactive or at rest) to provide a long outward stroke 137 (see FIG. 9) and a minimal inward stroke 139 (see FIG. 9). The step 306 of biasing the voice coil 112 and the drive shaft 130 may further comprise holding the voice coil 112 and the drive shaft 130 in the quiescent position with a biasing device 96 (see FIG. 5) comprising a coil spring 98 (see FIG. 4) or a foam piece 100 (see FIG. 5). The voice coil 112 is preferably biased axially in the magnetic gap 94 (see FIG. 5).

As further shown in FIG. 15, the method 300 comprises the step 308 of measuring an impact force using a load cell 144 (see FIG. 9) attached to a free end 142 (see FIG. 9) of the drive shaft 130 (see FIG. 9). The step 308 of measuring the impact force preferably comprises being able to measure greater than 100 pounds of impact force. The actual force level used during the method 300 may be determined by an operator and may be anywhere within the operating limits of the electrodynamic modal test impactor assembly 20 and the limits allowed by the structure 197 being tested and the method set-up.

The method 300 may further comprise exciting the structure 197 being tested at a frequency in a range of about 10 Hertz (Hz) to over 10 kiloHertz (kHz). The method 300 may further comprise powering the voice coil 112 with an electrical current in a range of about 0.1 amps (amperes) to about 10 amps (amperes).

EXAMPLES

Various electrodynamic modal impact tests were conducted using embodiments of the impactor assembly 20 (see FIG. 2A), system 10 (see FIG. 9), and method 300 (see FIG. 15) disclosed herein. The test results are set forth in FIGS. 10-14. The tests that were conducted are described below.

Example 1

The impactor assembly 20 (see FIG. 2A) was set up to impact against a rigid, steel-reinforced concrete wall that was three (3) feet thick and had a two (2) inch thick steel bar bolted onto its face. The surface of the steel bar was impacted. A half-sine pulse was used to drive the impactor assembly 20, and the amplitude of the pulse was varied, the initial distance of the tip on the impactor assembly 20 from the wall surface was varied, and the hardness of the material from which the tip was made was varied. The amplifier that was used was a small, 70 watt audio amplifier.

Figure 10:
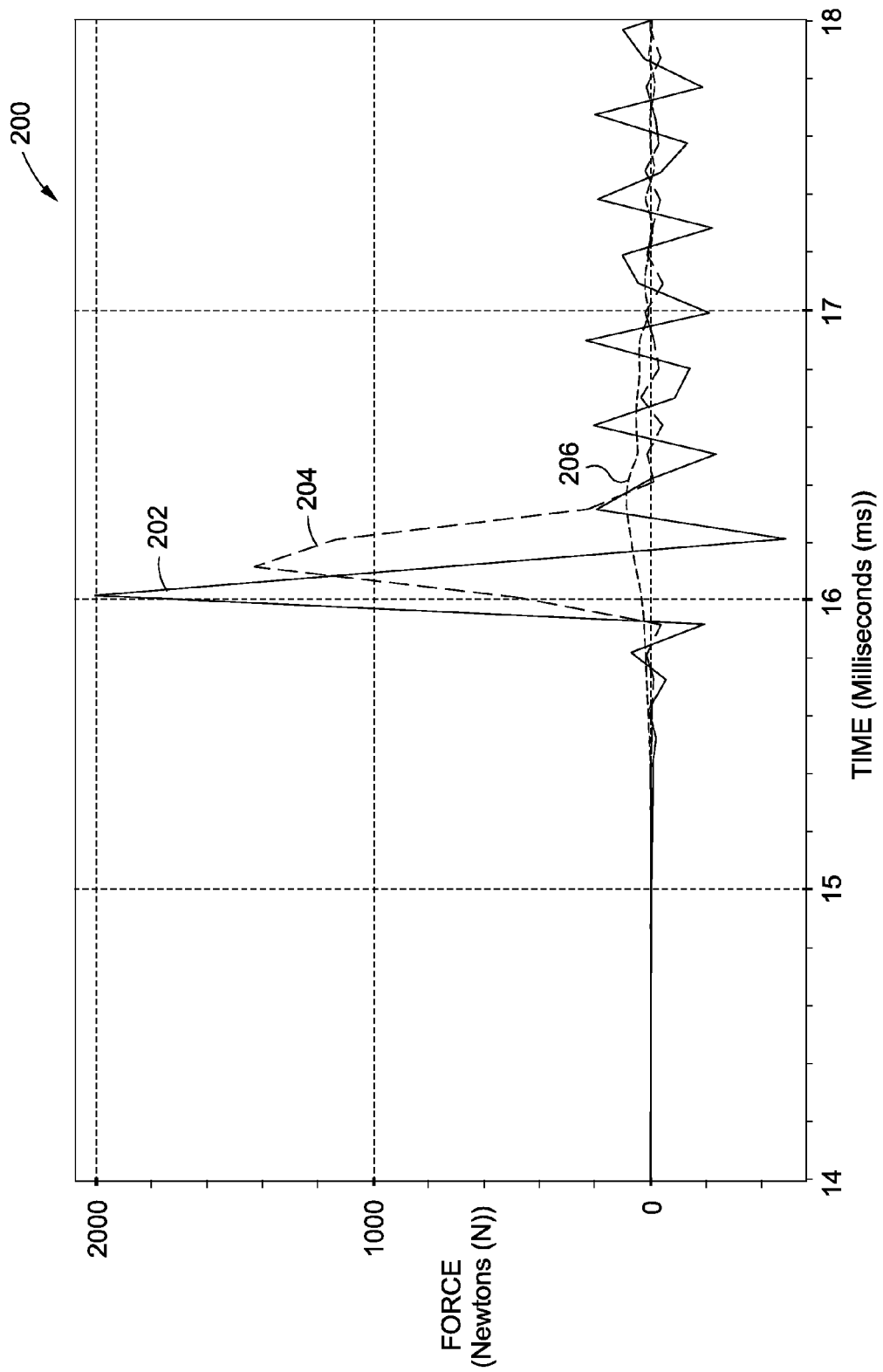
FIG. 10 is an illustration of a plot of the force versus time of maximum force measurements for a steel impact tip, a plastic impact tip, and a rubber impact tip using a small audio amplifier.

FIG. 10 is an illustration of a plot 200 of the force in Newtons (N) (1 pound equals 4.448 Newtons) versus time in milliseconds (ms) of maximum force measurements for a steel impact tip 202, a plastic impact tip 204, and a rubber impact tip 206 using the small, 70 watt audio amplifier. The maximum force measurements measured for the steel impact tip 202 was 450 pounds (impact period was 0.3 ms), for the plastic impact tip 204 was 300 pounds (impact period was 0.4 ms), and for the rubber impact tip was 20 pounds (impact period was 1.2 ms). Nearly a 4.1 difference in pulse length based on differences in hardness of the impact tips was seen. As was seen, for a given stiffness of a structure being impacted (in this case, maximum stiffness) the pulse length was a function primarily of impact tip hardness. Additional tests will show how the stiffness of the structure being impacted affects the pulse length and maximum amplitude attainable.

Example 2

The impactor assembly 20 (see FIG. 2A) was set up to impact against a rigid, steel-reinforced concrete wall that was three (3) feet thick and had a two (2) inch thick steel bar bolted onto its face. The surface of the steel bar was impacted. A half-sine pulse was used to drive the impactor assembly 20, and the amplitude of the pulse was varied, the initial distance of the tip on the impactor assembly 20 from the wall surface was varied, and the hardness of the material from which the tip was made was varied. The amplifier that was used was a small, 70 watt audio amplifier.

Figure 11:
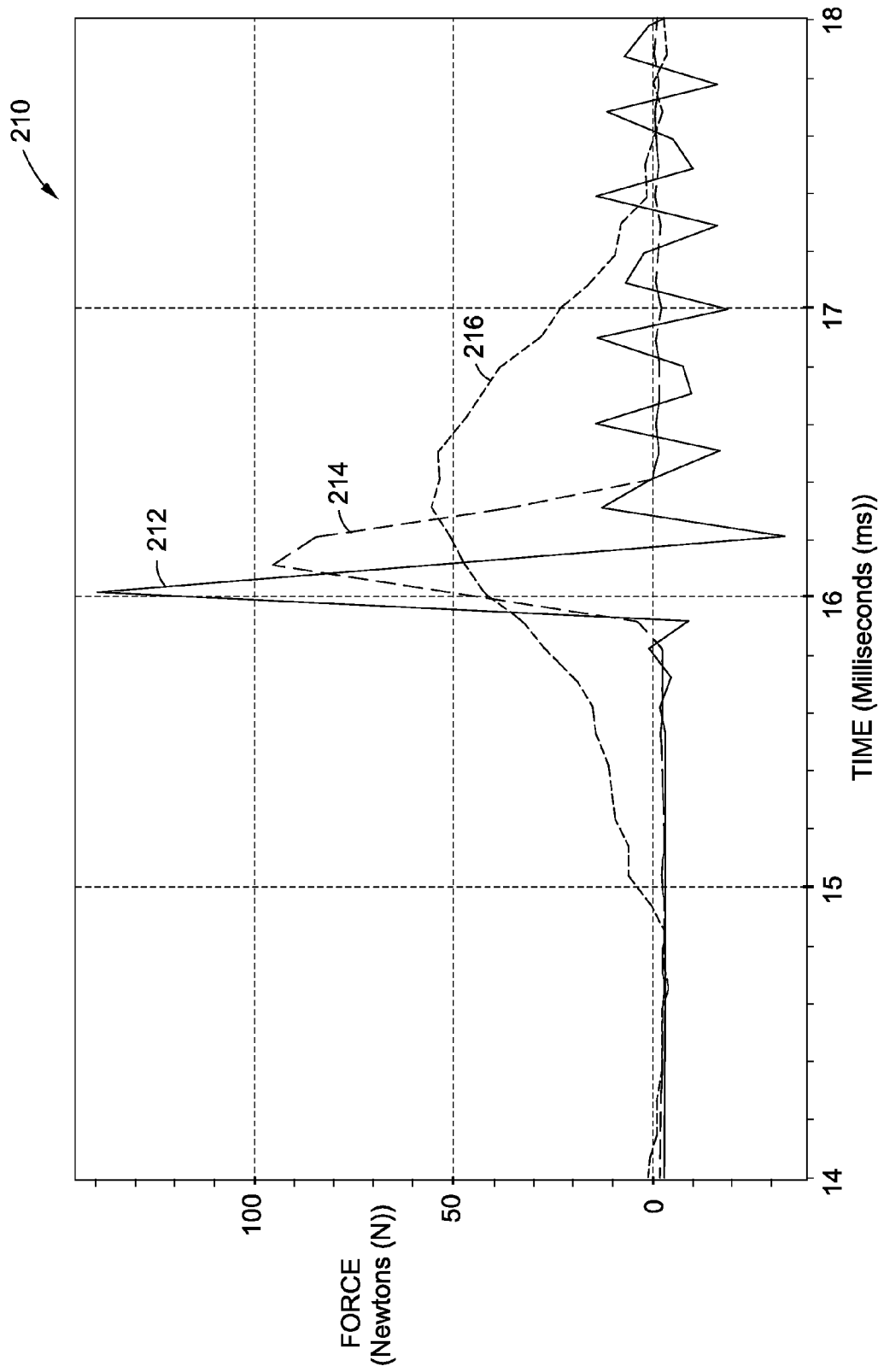
FIG. 11 is an illustration of a plot of the force versus time of minimum force measurements for a steel impact tip, a plastic impact tip, and a rubber impact tip using a small audio amplifier.

FIG. 11 is an illustration of a plot 210 of the force in Newtons (N) (1 pound equals 4.448 Newtons) versus time in milliseconds (ms) of minimum force measurements for a steel impact tip 212, a plastic impact tip 214, and a rubber impact tip 216 using the small, 70 watt audio amplifier. The minimum force measurements measured for the steel impact tip 212 was 32 pounds impact period was 3 ms), for the plastic impact tip 214 was 22 pounds (impact period was 0.5 ms), and for the rubber impact tip was 12 pounds (impact period was 3.5 ms). Nearly a 10.1 difference in pulse length based on differences in hardness of the impact tips was seen.

Example 3

The impactor assembly 20 (see FIG. 2A) was set up to impact against a rigid, steel-reinforced concrete wall that was three (3) feet thick and had a two (2) inch thick steel bar bolted onto its face. The surface of the steel bar was impacted. A half-sine pulse was used to drive the impactor assembly 20, and the amplitude of the pulse was varied, the initial distance of the tip on the impactor assembly 20 from the wall surface was varied, and the hardness of the material from which the tip was made was varied. The amplifier that was used was a medium, 150 watt audio amplifier.

Figure 12:
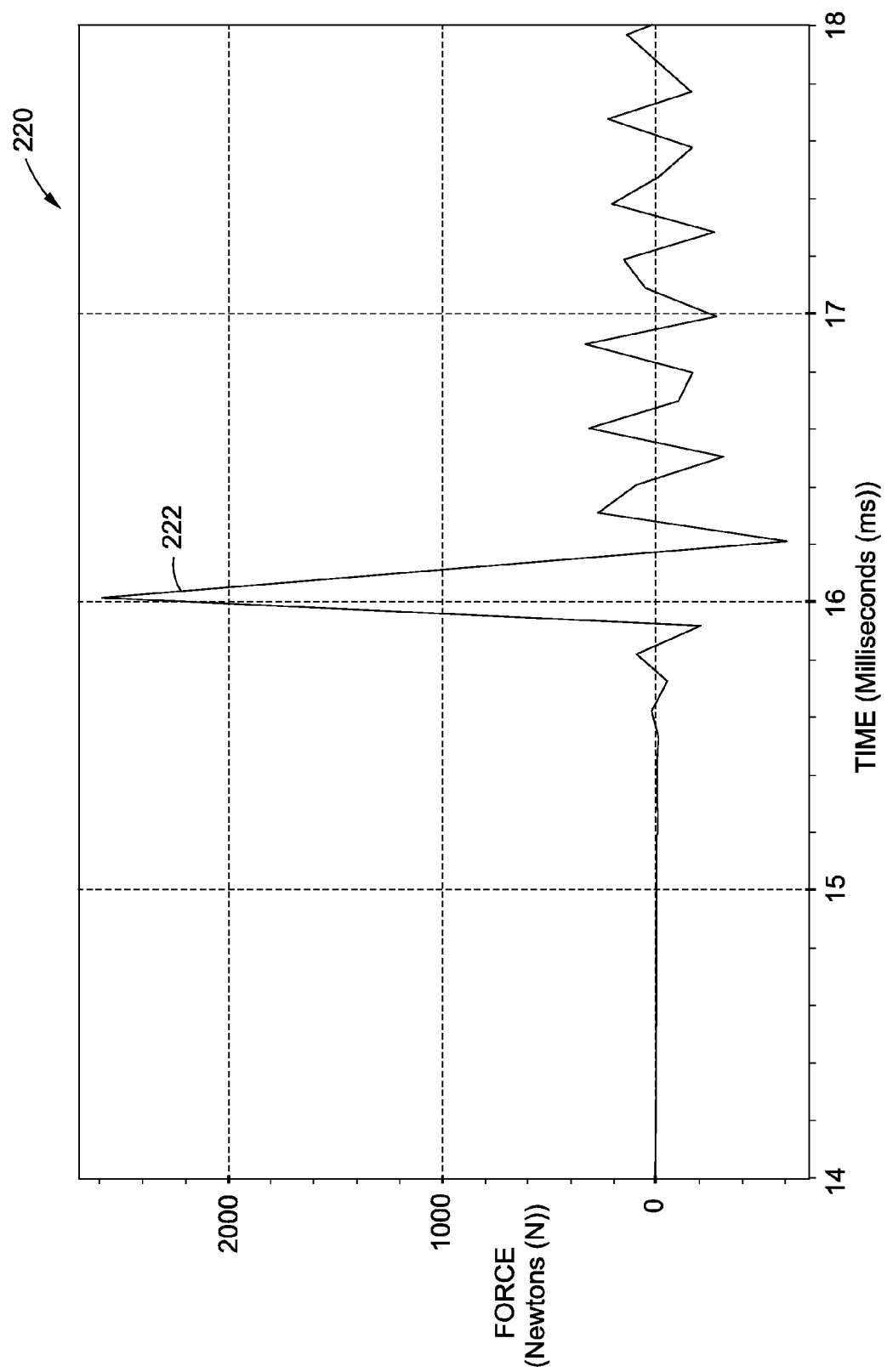
FIG. 12 is an illustration of a plot of the force versus time of maximum force measurements for a steel impact tip using a medium audio amplifier.

FIG. 12 is an illustration of a plot 220 of the force in Newtons (N) (1 pound equals 4.448 Newtons) versus time in milliseconds (ms) of maximum force measurement for the steel impact tip 222 using a medium audio amplifier. The maximum force measurements measured for the steel impact tip 222 was 550 pounds (impact period was 0.3 ms).

Example 4

The impactor assembly 20 (see FIG. 2A) was set up to impact against a rigid, steel-reinforced concrete wall that was three (3) feet thick and had a two (2) inch thick steel bar bolted onto its face. The surface of the steel bar was impacted. A half-sine pulse was used to drive the impactor assembly 20, and the amplitude of the pulse was varied, the initial distance of the tip on the impactor assembly 20 from the wall surface was varied, and the hardness of the material from which the tip was made was varied. The amplifier that was used was a large, 600 watt audio amplifier.

Figure 13:
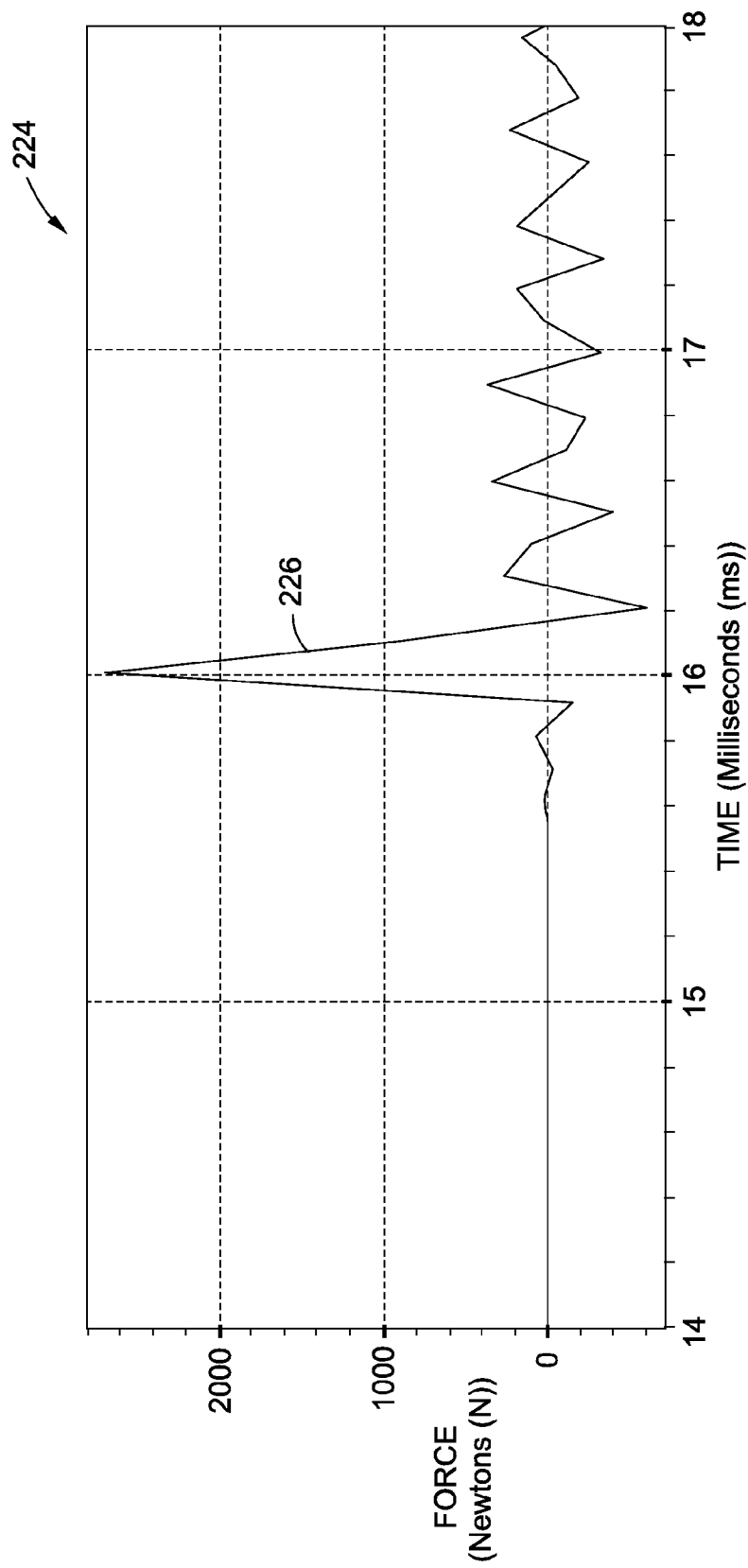
FIG. 13 is an illustration of a plot of the force versus time of maximum force measurements for a steel impact tip using a large audio amplifier.

FIG. 13 is an illustration of a plot 224 of the force in Newtons (N) (1 pound equals 4.448 Newtons) versus time in milliseconds (ms) of maximum force measurements for a steel impact tip 226 using a large audio amplifier. The maximum force measurement measured for the steel impact tip 226 was 600 pounds (impact period was 0.3). Much higher force levels could have been achieved, but that would have caused double impacts under the conditions, which was something to be avoided during actual tests.

Example 5

The impactor assembly 20 (see FIG. 2A) was set up to impact against a typical aerospace structure, hanging free-free on springs, to provide known boundary conditions. As used herein, "free-free" refers to a support method that allows the supported structure to move freely in three (3) degrees of freedom in both translation (the first "free") and rotation (the second "free"), and may be used to imply that the supported structure is not "fixed", "clamped" or "pinned" in such a way as to inhibit its mobility, and these terms may be used to designate a structure's "boundary conditions". A half-sine pulse was used to drive the impactor assembly 20. The amplitude of the pulse was varied, to ensure suitable response of the structure being tested was seen, and the initial distance of the tip on the impactor assembly 20 from the surface of the structure being tested was varied to ensure the structure did not swing back into the impactor assembly 20 and did not get double impacts. The hardness of the material from which the tip was made was chosen to ensure that the entire frequency range of interest was excited and the maximum usable force was attained. The amplifier that was used was a small, 70 watt amplifier.

Figure 14:
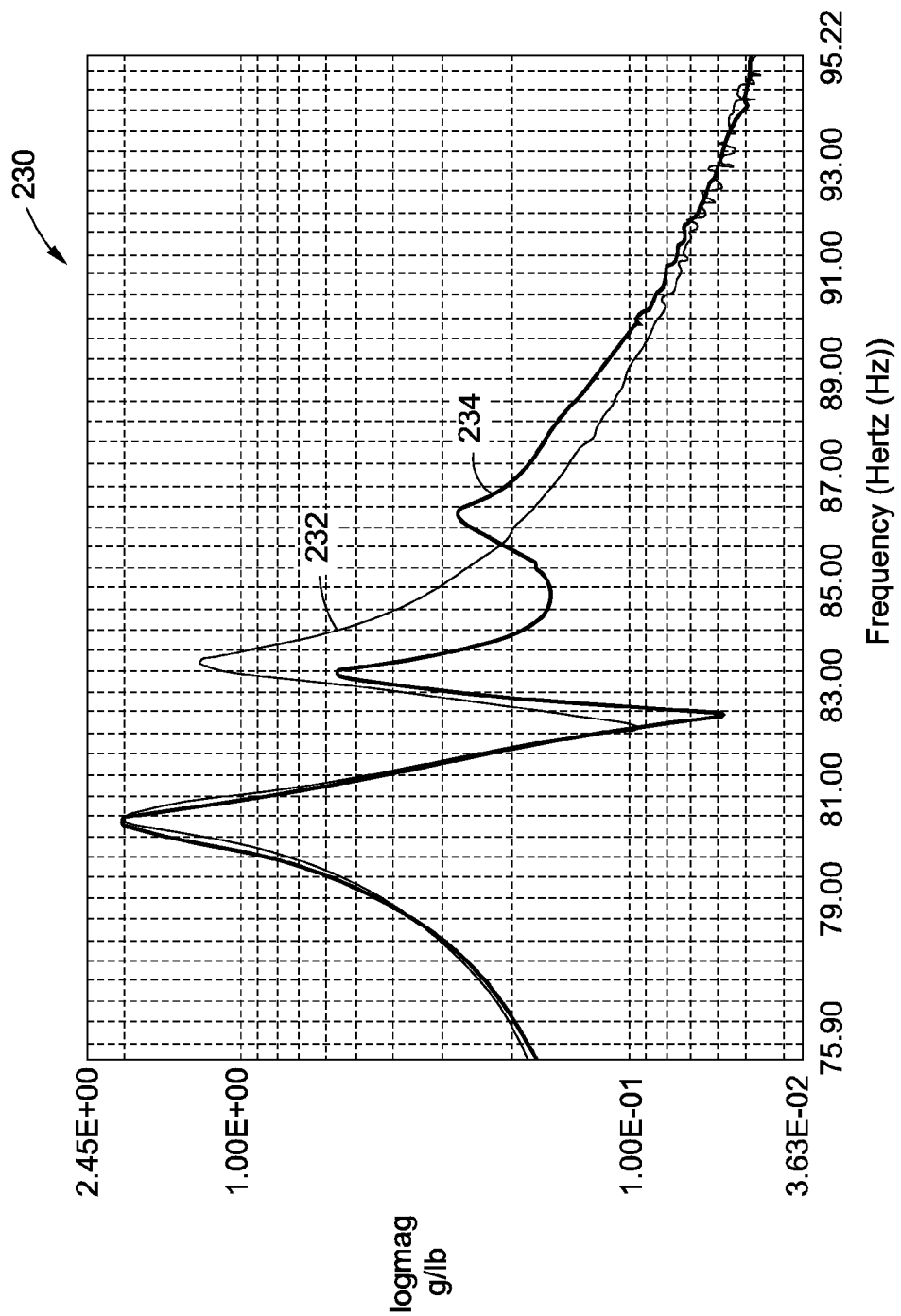
FIG. 14 is an illustration of a plot of the acceleration response of a structure due to a "normalized" (i.e., response divided by force) force impact versus frequency of measurements for manual hammer impacts and automated impacts using the system and method of the disclosure; and, FIG. 15 is an illustration of a flow diagram illustrating one of the embodiments of a method of the disclosure.

FIG. 14 is an illustration of a plot 230 of the acceleration response of the structure being tested due to a "normalized" (i.e., response divided by force) force impact in log mag (g/lb (g's/pound)) versus frequency in Hertz (Hz (cycles per second)) of measurements for manual hammer impacts and automated impacts using the impactor assembly 20 (see FIG. 2A). The quality of data collected from manual hammer impacts 234 was compared to the quality of data collected from impacts 232 using the impactor assembly 20 (see FIG. 2A) disclosed herein. The extra peak in the data from the manual hammer test was indicative of non-linearities induced due to inconsistent impacts during the measurement. The operator of the hammer impacted the test structure as consistently as possible, but still ended up with corrupted data.

Disclosed embodiments of the impactor assembly 20 (see FIG. 2A), system 10 (see FIG. 9) and method 300 (see FIG. 15), as compared to existing modal impact test systems and methods, may improve data quality, may reduce test times by minimizing the time between impacts which is needed when a manual operation is used to try to control a hammer, and may eliminate double impacts, which are unacceptable from a data standpoint and almost unavoidable with a hammer. In addition, disclosed embodiments of the impactor assembly 20 (see FIG. 2A), system 10 (see FIG. 9) and method 300 (see FIG. 15), combine a method for pulse shape and amplitude control, together with the impactor assembly 20, that is small and compact in size and support and is adjustable to fit the structure 197 (see FIG. 9) to be tested or under test. Moreover, disclosed embodiments of the impactor assembly 20 (see FIG. 2A), system 10 (see FIG. 9) and method 300 (see FIG. 15), provide an impactor assembly 20 that may be designed as a low duty cycle impactor, so it uses very small voice coil windings 120 (see FIG. 6) which would otherwise be destroyed by continuous current flow at the levels intended.

In addition, disclosed embodiments of the impactor assembly 20 (see FIG. 2A), system 10 (see FIG. 9) and method 300 (see FIG. 15), provide an impactor assembly 20 where the drive shaft 130 (see FIG. 2A) may be integrally machined with the armature support 126 (see FIG. 2A), thus eliminating parts and providing structural integrity, and provide an impactor assembly 20 where the drive shaft 130 (see FIG. 2A) may preferably be supported in support elements 174 (see FIGS. 8A-8B), comprising first support element 174a, such as in the form of bushing 175a, and second support element 174b, such as in the form of bushing 175b, thus allowing long throws or long outward strokes 137 (see FIG. 9) of the voice coil 112 (see FIG. 2A) and drive shaft 130 (see FIG. 2A), which may help to prevent multiple impacts (i.e. no flexures constraining axial motion).

Further disclosed embodiments of the impactor assembly 20 (see FIG. 2A), system 10 (see FIG. 9) and method 300 (see FIG. 15), provide an impactor assembly 20 (see FIG. 2A) that uses permanent magnets 70, such as Neodymium-Boron-Iron magnets, which may be used to provide very high flux densities in the magnetic gap 94 (see FIG. 5) while maintaining a compact design (total package size is approximately 4 inches in diameter and 6 inches long), and provide a design that allows the impactor assembly 20 to be supported directly on a small, articulating mounting device 180 (see FIG. 1A) that may provide complete freedom of position and orientation of the impactor assembly 20 with respect to a structure 197 (see FIG. 9) to be tested or being tested. Moreover, disclosed embodiments of the impactor assembly 20 (see FIG. 2A), system 10 (see FIG. 9) and method 300 (see FIG. 15), provide an impactor assembly 20 (see FIG. 2A) capable of producing over 600 pounds of force, and capable of exciting structures well into the kiloHertz (kHz) frequency range, such as for example, exciting the structure being tested at a frequency in a range of about 10 Hertz (Hz) to over 10 kiloHertz (kHz). The impactor assembly 20, system 10, and method 300 may be used to impart a relatively mild force impact 155 (see FIG. 9) to a discrete location on a structure 197 being tested in order to monitor a response of the structure 197 over its entire surface. The modes of vibration of the structure 197 may be measured.

In addition, disclosed embodiments of the impactor assembly 20 (see FIG. 2A), system 10 (see FIG. 9), and method 300 (see FIG. 15), as compared to existing modal impact test systems and methods, may have an increased controllability over the impact direction, may have an increased adjustability, may have the ability to couple an external drive signal via impact signal wires into the impactor assembly 20, and may avoid or eliminate contamination of test data by not using contact points between the structure 197 (see FIG. 9) to be tested or being tested and the impactor assembly 20 (e.g., avoids placing an impact device such as a solenoid on the structure to be tested or being tested). The impactor 20 disclosed herein is not attached or in contact with the structure 197 being tested during the electrodynamic modal impact testing other than contact of the impact tip 154 during the actual impact.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. An electrodynamic modal test impactor system comprising:
    a controller device;
    an impactor assembly coupled to the controller device, the impactor assembly comprising:
        a housing;
        a permanent magnet positioned within the housing;
        a voice coil positioned within the housing in a magnetic gap of a magnetic yoke housing, the voice coil being driven by the controller device;
        a drive shaft having a first end and a second end, the first end of the drive shaft being a free end and being attached to a load cell positioned outside the housing, and the second end of the drive shaft inserted into a central opening of an armature support attached to the voice coil, the drive shaft extending from the voice coil and the permanent magnet to the load cell, and the drive shaft being driven by the voice coil; and,
        a biasing device positioned within the magnetic yoke housing.

2. The system of claim 1 wherein the controller device comprises an audio amplifier device.

3. The system of claim 1 wherein the housing comprises a first housing portion and a second housing portion, the first housing portion comprising a cap portion and a base portion, and the second housing portion comprising the magnetic yoke housing.

4. The system of claim 1 wherein the permanent magnet is coupled between a magnetic yoke base plate and a magnetic yoke center pole and is surrounded by a magnetic yoke outer pole, wherein the permanent magnet, the magnetic yoke base plate, the magnetic yoke center pole, and the magnetic yoke outer pole comprise a magnet assembly housed within the magnetic yoke housing.

5. The system of claim 1 wherein the voice coil comprises a winding wound around an exterior of an armature support, the winding comprising a wire having a gauge measurement of 30 gauge or greater.

6. The system of claim 1 wherein the armature support is integrally machined with the drive shaft.

7. The system of claim 1 wherein the drive shaft is supported by two or more support elements comprising bushings each having an opening corresponding to an outer diameter of the drive shaft.

8. The system of claim 1 wherein the load cell is attached to an impact tip.

9. The system of claim 1 wherein an integral force measuring device comprising one or more strain gauges and one or more strain gauge wires is attached to the drive shaft and is used in place of the load cell, and an impact tip is attached directly to the free end of the drive shaft.

10. The system of claim 1 wherein the biasing device comprises two coil springs or two foam pieces.

11. The system of claim 1 further comprising a connector comprising a plurality of impact signal wires, the connector attached between the controller device and the impactor assembly.

12. The system of claim 1 further comprising an articulating mounting device on which the impactor assembly is mounted.

13. The system of claim 1 further comprising a computer device and/or processor unit to review and analyze electrodynamic modal impact test measurements measured with the system.

14. An automated electrodynamic modal test impactor system comprising:
    an audio amplifier;
    an impactor assembly coupled to the audio amplifier via a plurality of impact signal wires, the impactor assembly comprising:
        a housing comprising a first housing portion and a second housing portion, the second housing portion comprising a magnetic yoke housing;
        a magnet assembly housed within the magnetic yoke housing, the magnet assembly comprising a permanent magnet coupled between a magnetic yoke base plate and a magnetic yoke center pole and surrounded by a magnetic yoke outer pole;
        a biasing device positioned within the magnetic yoke housing;
        a voice coil positioned within the housing in a magnetic gap of the magnetic yoke housing, the voice coil being driven by the audio amplifier;
        a drive shaft having a first end and a second end, the first end of the drive shaft being a free end and being attached to a load cell positioned outside the housing, and the second end of the drive shaft inserted into a central opening of an armature support attached to the voice coil, the drive shaft extending from the voice coil and the permanent magnet to the load cell, and the drive shaft being driven by the voice coil; and,
        an impact tip attached to the load cell;
    an articulating mounting device on which the impactor assembly is mounted; and,
    a computer device to review and analyze electrodynamic modal impact test measurements measured with the system.

15. The system of claim 14 wherein an integral force measuring device comprising one or more strain gauges and one or more strain gauge wires is attached to the drive shaft and is used in place of the load cell, and an impact tip is attached directly to the free end of the drive shaft.

16. A method of performing electrodynamic modal impact tests, the method comprising the steps of:
    imparting short duration force impacts of between about 1 millisecond to about 10 milliseconds in duration on a structure being tested for dynamic modal response;
    centering a voice coil within a magnetic gap;
    biasing the voice coil and a drive shaft driven by the voice coil, in a quiescent position to provide an outward stroke and an inward stroke, the drive shaft having a first end and a second end, the first end of the drive shaft being a free end and being attached to a load cell positioned outside the housing, and the second end of the drive shaft inserted into a central opening of an armature support attached to the voice coil, the drive shaft extending from the voice coil and the permanent magnet to the load cell; and, measuring an impact force using the load cell.

17. The method of claim 16 wherein biasing the voice coil and the drive shaft further comprises holding the voice coil and the drive shaft in the quiescent position with a biasing device comprising a coil spring or a foam piece.

18. The method of claim 16 wherein the measuring step comprises measuring greater than 100 pounds of impact force.

19. The method of claim 16 further comprising exciting the structure being tested at a frequency in a range of 10 Hertz (Hz) to 10 kiloHertz (kHz).

20. The method of claim 16 further comprising powering the voice coil with an electrical current in a range of 0.1 amps (amperes) to 10 amps (amperes).

\* \* \* \* \*